US007001892B1

(12) United States Patent
Chmielewski et al.

(10) Patent No.: US 7,001,892 B1
(45) Date of Patent: Feb. 21, 2006

(54) PHARMACEUTICAL MATERIALS AND METHODS FOR THEIR PREPARATION AND USE

(75) Inventors: Jean A. Chmielewski, Lafayette, IN (US); Bart E. Kahr, Seattle, WA (US); Jerry Lewis, Carmel, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/018,043

(22) PCT Filed: Jun. 12, 2000

(86) PCT No.: PCT/US00/16140

§ 371 (c)(1),
(2), (4) Date: May 21, 2002

(87) PCT Pub. No.: WO00/76480

PCT Pub. Date: Dec. 21, 2000

Related U.S. Application Data

(60) Provisional application No. 60/138,912, filed on Jun. 11, 1999.

(51) Int. Cl.
*A61K 31/7016* (2006.01)
*A61K 47/26* (2006.01)
(52) U.S. Cl. .................................. 514/53; 536/123.13
(58) Field of Classification Search .................. 514/53; 536/123.13
See application file for complete search history.

(56) References Cited

U.S. PATENT DOCUMENTS

| 4,501,726 A | 2/1985 | Schroder et al. |
| 4,713,249 A | 12/1987 | Schroder |
| 5,015,480 A | 5/1991 | Childers et al. |
| 5,075,291 A | 12/1991 | DuRoss |
| 5,506,203 A | 4/1996 | Backstrom et al. |

FOREIGN PATENT DOCUMENTS

| EP | 0 052 413 | * | 5/1982 |
| EP | 0 052 413 A2 | | 5/1982 |
| EP | 0 119 480 A | | 9/1984 |
| EP | 0 314 469 A | | 5/1989 |
| EP | 0 435 450 A | | 7/1991 |
| EP | 0 629 393 A | | 12/1994 |
| GB | 2 160 100 A | | 12/1985 |
| WO | WO 95/24183 | | 9/1995 |
| WO | WO 97/21838 A | | 6/1997 |
| WO | WO 98/42367 | | 10/1998 |
| WO | WO 00/076480 A3 | | 12/2000 |

OTHER PUBLICATIONS

Beavis, Ronald C. et al. Epitaxial Protein Inclusion in Sinapic Acid Crystals, J. Phys. D: Appl. Phys. 26 (1993) 442-447.

Borman, Stu. Biochemical Applications of Mass Spectrometry Take Flight, C&EN, Jun. 19, 1995, 23-32.

Carpenter, J.F. and Crowe, J.H. Infrared Spectrosopic Studies of the Interaction of Carbohydrates with Dried Proteins, Biochemistry, 1989, pp. 3916-3922, vol. 28.

Carpenter, J.F, et al. Separation of Freezing- and Drying-induced Denaturation of Lyophilized Proteins by stress-specific stabilization: I. Enzyme Activity and Calorimetric Studies. Arch. Biochem. Biophys., 1993, pp. 456-464, vol. 303.

Chmielewski, Jean, et al. Single-Crystal Matrix Isolation of Biopolymers, J. Am. Chem. Soc., Oct. 29, 1997, pp. 10565-10566, vol. 119, No. 43.

Goke, R., et al. Exendin-4 is a High Potency Agonist and Truncated Exendin-(9-39)-amide an Antagonist at the Glucagon-like Peptide 1-(7-36)-amide Receptor of Insulin-secreting Beta-cells. J.Biol. Chem., Sep. 15, 1993, pp. 19650-19655, 268 (26).

Hillenkamp, Franz, et al. Matrix-Assisted Laser Desorption/Ionization Mass Spectrometry of Biopolymers, Analytical Chemistry, Dec. 15, 1991, pp. 1193A-1283A, vol. 63, No. 24.

Izutsu, K., et al. The Effects of additives on the stability of freeze-dried β-galactosidase stored at elevated temperatures. Int. J. Pharm:, 1991, pp. 137-146, vol. 71.

Izutsu, K., et al. Decreased protein-stabilzing effects of cryoprotectants due to crystallization. Pharm. Res., 1993, pp. 1232-1237, vol. 10.

Kurimoto, Miki et al. Kinetic Stabilization of Biopolymers in Single-Crystal Hosts: Green Fluorescent Protein in α-Lactose Monohydrate, J. Am. Chem. Soc. 1999, vol. 121, pp. 6952-6953.

Malkin, A.J. et al. Mechanisms of Growth for Protein and Virus Crystals, Nature Structural Biology, vol. 2, No. 11, Nov., 1995.

(Continued)

*Primary Examiner*—Leigh C. Maier
(74) *Attorney, Agent, or Firm*—Woodard, Emhardt, Moriarty, McNett & Henry LLP

(57) ABSTRACT

Pharmaceutical compositions comprising crystals of a pharmaceutically-acceptable crystal lattice component, and an active pharmaceutical ingredient different from and included within the crystal lattice component in a growth-sector specific orientation. The crystals are prepared using components and methods which yield crystals having suitable purity and efficacy for use in administering the active pharmaceutical ingredients to a patient. The crystals are typically combined with adjuvants such as excipients, diluents or carriers, and are preferably formulated into tablets, capsules, suspensions, and other conventional forms containing predetermined amounts of the pharmaceuticals. Also provided are methods for preparing the crystals, and methods for storing and administering the active pharmaceutical ingredient either included within the crystals or upon reconstitution of the crystals to a solution.

8 Claims, 2 Drawing Sheets

OTHER PUBLICATIONS

Powers, H.E.C. Sucrose Crystals: Inclusions and Structure, Sugar Technol Rev., 1 (1969/70) 85-190.

Rasimas, J.P. et al. Measuring Self-Assembly in Solution: Incorporation and Dynamics of A "Tailor-Made Impurity" in Precrystalline Glucose Aggregates, Department of Chemistry and Department of Chemical Engineering, Michigan State University, East Lansing, Michigan, J. Phys. Chem. (1996) vol. 42 pp 17034-17040.

Strupat, K. et al. 2.5-Dihydroxybenzoic Acid: A New Matrix For Laser Desorption-Ionization Mass Spectrometry, International Journal of Mass Spectrometry and Ion Processes, 111 (1991) 89-102.

Visser, R.A., et al. A Natural Crystal Growth Retarder in Lactose. Milk Diary J., 1980, pp. 255-275, vol. 34.

* cited by examiner

PHARMACEUTICAL MATERIALS AND METHODS FOR THEIR PREPARATION AND USE

This Application claims the benefit of Provisional Application No. 60/138,912 filed on Jun. 11, 1999.

BACKGROUND OF THE INVENTION

1. Field of the Invention

The present invention relates to pharmaceutical formulations involving the inclusion of an active pharmaceutical ingredient ("API") in a pharmaceutically-acceptable single crystal matrix. More particularly, the crystals contain growth-sector specific, oriented inclusions of active pharmaceutical ingredients which are isolated. The active pharmaceutical ingredients have higher stability and shelf-life, and can be delivered in conventional dosage forms. This invention has general application to active pharmaceutical ingredients, and in one aspect has particular application to biopharmaceuticals. As used herein, the term "biopharmaceuticals" is used to refer to a subset of API's which are polymeric in nature, including for example, proteins, polypeptides, enzymes, immunoglobulins, polynucleic acids, and plasmids.

2. Description of the Prior Art

There is a continuing need for pharmaceutical compositions which are capable of maintaining the quality and efficacy of the API during storage and delivery. The loss of potency of an API is a critical concern in assuring that viable, effective drugs are delivered to patients. It is similarly desirable to have formulations which do not require special package or handling. Further, it remains a constant goal to provide active pharmaceutical ingredients in a form which facilitates their use by the consumer, such as though convenient dosage forms. The present invention addresses these and other issues concerning pharmaceutical compositions and formulations.

Although not limited to biopharmaceuticals, the usefulness of the present invention is well exemplified with respect to biopharmaceuticals, many of which demonstrate the problems encountered in prior-art approaches. Ensuring long-term stability and maintaining activity of biopharmaceuticals is a prevalent concern. The chemical complexity and conformational fragility of protein drugs, for example, make them highly susceptible to both physical and chemical instabilities and threaten their emergence into the marketplace. Denaturation, adsorption with container walls, aggregation, and precipitation can result from non-covalent interactions between a drug and its environment. Insulin, for instance, has been shown to adsorb onto the surfaces of glass and plastic containers, and to have interactions at air-water interfaces, leading to denaturation, aggregation and precipitation. For example, upon demonstration human growth hormone (HGH) forms dimers and higher molecular weight aggregates, and glucagon in solution has been shown to readily gel or aggregate when subjected to mechanical stress.

As a further example, researchers have distinguished nine major reaction mechanism by which proteins degrade, including hydrolysis, imide formation, deamidation, isomerization, racemization, diketopiperazine formation, oxidation, disulfide exchange, and photodecomposition. The rates of these deleterious processes depend in large measure on the protein and its environment. The primary chemical degradation products of glucagon, for example, include oxidation of Met (27), deamidation of Gln (24), and acid-catalyzed hydrolysis at Asp (9), Asp (15) and Asp (21). HGH undergoes chemical decomposition via oxidation at Met (14) and deamidation at Asn (149).

A critical challenge of product development science in the pharmaceutical industry therefore has been devising formulations that maintain the stability of the active pharmaceutical ingredient over an acceptable shelf-life. This has been especially difficult to achieve for certain API's which are unstable in solution or with respect to many common formulation processes. Developing techniques for stabilization and storage looms as a great impediment to the pharmaceutical industry. Formulation scientists have consequently used a variety of techniques to enhance the stability of API's while maintaining other important product characteristics such as biocompatibility, absorption, pharmacokinetics, efficacy and excretion.

One technique used in formulating biopharmaceuticals has been lyophilization of the biopharmaceutical solution in the presence of excipients, buffers and/or bulking agents. However, even lyophilized preparations must typically be stored under refrigeration, a requirement which is neither technically nor economically feasible in many markets and inhibits flexibility of patient use. There has therefore been a continuing demand for formulations of many biopharmaceuticals which would permit their storage at ambient temperatures. This would permit more rapid development of products, increasing flexibility in shipping, storing and carrying the drug products, and allowing introduction and use of such products in markets where refrigeration is too costly. Moreover, the increased stabilization of biopharmaceuticals would naturally improve the general use of the biopharmaceuticals where shelf life is an important consideration, whether or not refrigeration or other concerns are at issue.

The prior art use of excipients in the lyophilization of biopharmaceuticals has been directed away from inclusion of the biopharmaceuticals in single crystals in the manner of the present invention. It has been widely assumed that amorphous glasses are critical in the stabilization of biopharmaceuticals by such excipients in lyophilized form, and it has been suggested that the drug molecules must exist in amorphous regions between the crystalline domains. See, e.g., M. J. Pikal, "Freeze Drying of Proteins", to be published in Peptide and Protein Delivery, $2^{nd}$ Ed., V. H., L. Lee, Marcel Dekker, Prepint, 1995. Implicit in this reasoning is the conclusion that the biopharmaceuticals could not exist as guests within single crystals.

In the process of lyophilization, typically an aqueous solution containing a biopharmaceutical with a limited amount of excipient(s) is frozen and then dried under vacuum to produce solids of sufficient stability for storage and distribution. Excipients are added to prevent blow out of the product, to provide stability during lyophilization and/or dissolution, and to enhance compatibility for parenteral use. Various excipients used with lyophilization have included salts, metal ions, polyalcohols, surfactants, reducing agents, chelating agents, other proteins, amino acids, fatty acids, and phospholipids. The more frequently used excipient include mannitol, alanine, glycine, sorbitol, lactose, arginine, and maltose. The results obtained with such excipients, however, have usually been inconsistent. Most lyophilized biopharmaceuticals are amorphous powders that have not specific structure, and as a result, the amount and location of the incorporated biopharmaceutical varies widely for the product particles. Also, they are typically readily dissolved, rendering them unsuitable for use as a sustained-release material. Further, there is no isolation of the pharmaceutical molecules from the environment or one another, leaving them susceptible to degradation by various mechanisms. Studies have shown that lyophilization of excipients can typically damage proteins rather than protect them. See, e.g., J. F. Carpenter, J. H. Crowe, "Infrared spectroscopic studies of the interaction of carbohydrates with dried proteins", Biochemistry 1989, 28, 3916–3922; J. F. Carpenter, S. Prestrelski, T. Arakawa, "Separation of freezing- and drying-induced denaturation of lyophilized proteins by stress-specific stabilization: I. Enzyme activity and calorimetric studies," Arch. Biochem. Biophys. 1993, 303, 456–464. K. Izutsu, S. Yoshioka, Y. Takeda, "The effects of additives on the stability of freeze-dried β-galactosidase stored at elevated temperatures", Int. J. Pharm. 1991, 71, 137–146. K. Izutsu, S. Yoshioka, T. Teroa, "Decreased protein-stabilizing effects of cryoprotectants due to crystallization", Pharm. Res. 1993, 10, 1232–1237.

Crystallized pharmaceuticals have been used in some instances, but there have been inherent limitations. Some API's, e.g. insulin, can be crystallized themselves, and are useful in that form for administration to patients. However, the majority of biopharmaceuticals either do not crystallize or the crystallization is very difficult, particularly on a commercial scale. Further, crystallization procedures are limited to the use of pharmaceutically-acceptable ingredients and process conditions that do not adversely affect the active pharmaceutical ingredient, thus further constraining the ability to obtain desired microcrystalline suspensions.

The fact that macromolecules are routinely isolated in sub-millimolar concentrations in a variety of crystals is known. See, e.g., K. Strupat, M. Karas, F. Hillenkamp, Int. J. Mass Spec. Ion Proc., 111, 89–102, 1991. Also, certain aromatic acids have been employed as hosts for biopolymer guests in crystals for use in matrix-assisted laser desorption ionization (MALDI) mass spectrometry, but not for the purposes of the present invention. See, Review by F. Hillenkamp, M. Karas, R. C. Beavis, B. T. Chait, Anal. Chem, 63, 1193A–1203A; S. Borman, Chem. Eng. News, 23–25, Jun. 19, 1995. However, crystallization conditions in these studies were optimized for characterization of the incorporated biopolymers. There were no investigations into optimizations that would be relevant to pharmaceutical preparations or operations such as homogeneity of the concentration of the inclusions, process scale-up, process robustness, chemical and physical stability of the preparations, suspendability in biocompatible solutions, preservative requirements and compatibility, container/closure system compatibility, and pharmacokinetic profiles.

The difficulty in obtaining suitable single crystals of some biopolymers has encouraged structural chemists to partially orient such molecules with electric, magnetic, or flow fields, by dissolution in liquid crystals or stretched gels, and as monolayers. In a similar effort, the isolation of biopolymers in a single crystal matrix has recently been studied in an effort to use such crystals for structural analysis of the biopolymers. Such isolation technique is described in "Single Crystal Matrix Isolation of Biopolymers," J. Chmielewski, J. J. Lewis, S. Lovell, R. Zutshi, P. Savickas, C. A. Mitchell, J. A. Subramony, and B. Kahr, J. Am. Chem. Soc. 1997, 119, 10565–10566. However, this article simply demonstrates that certain biopolymers are oriented by the host lattice, and the article suggests the use of such crystals for analyzing spectral anisotropies in biological molecules which could not otherwise be crystallized. This article does not discuss or suggest the use of this technique for enhancement of stability or sustained release of pharmaceuticals, or their administration to patients. Further, the proteins studied were not a pharmaceutical interest, the crystal materials described in this article, namely phthalic acid, gentistic acid and sinapic acid, were not selected or evaluated for biocompatibility, and the crystal sizes were not optimized for particular routes of administration. Therefore, the produced crystals with included biopolymers would not be suitable for administration to patients.

Other prior art procedures have required the use of polymers that are difficult to prepare, require harsh preparation conditions that can be harmful to the API's, and yield inconsistent results. For example, U.S. Pat. No. 5,075,291 describes a process for preparing a uniformly-dispersed, pharmaceutically-active material in a crystalline sugar alcohol matrix. However, this process requires the addition of the API into a molten sugar alcohol with considerable mechanical agitation. Many API's and virtually all biopharmaceuticals would not be stable in the extreme temperature of 110° C. and the physical stresses of a high-shear vortex mixer used for agitation. The present invention does not require these extremes of temperature and physical agitation. Also, the process of the present invention slowly includes the API into the growing crystal lattice in specific growth sectors, instead of homogeneous mixing and entrapping of the active pharmaceutical ingredient in a viscous melt.

SUMMARY OF THE INVENTION

In one aspect, the present invention relates to pharmaceutical compositions comprising single crystals of a pharmaceutically-acceptable crystal lattice component, and an active pharmaceutical ingredient different from and included within the crystal lattice component in a growth-sector specific orientation. The crystals are prepared using components and methods which yield crystals having suitable purity and efficacy for use in administering the API's to a patient. The crystals may be coated or combined with adjuvants such as excipients, diluents or carriers, and are preferably formulated into tablets, capsules, suspensions, and other conventional forms containing dosage amounts of the API's. Alternatively, the crystals are prepared as depot formulations which may be administered, as by subcutaneous injection or implantation, to provide a long-term payout or sustained release of the active pharmaceutical ingredient. The present invention further provides methods for preparing the crystals and for storing and administering the active pharmaceutical ingredient either in crystal form or upon reconstitution to a solution.

Accordingly, it is an object of the present invention to provide single crystals which include API's in a growth-sector specific orientation. It is a feature of the invention that the API's are included at predictable, uniform concentrations that permit use of the crystals in formulating dosage amounts of the API's.

Another object of the present invention is to provide compositions comprising API's included in single crystals to provide improved stability and shelf-life. The active pharmaceutical ingredients may therefore be stored for extended periods of time prior to use either as crystals or as reconstituted solutions.

It is a further object of the present invention to provide single crystals with included API's to provide quick, delayed-release or sustained-release formulations for flexibility in pharmacokinetic profiles in delivery of the API's to patients.

Another object of the present invention is to provide pharmaceutical delivery units including an amount of single crystals sufficient to provide a dosage amount of the included active pharmaceutical ingredient. Alternatively, the pharmaceutical delivery units include a quantity of crystals sufficient to provide a prolonged payout of the active pharmaceutical ingredient. The crystals may be coated or uncoated, and may be combined with various pharmaceutical adjuvants including excipients, diluents and carriers.

A further object of the present invention is to provide methods for preparing compositions comprising single crystals with growth-sector specific inclusions of API's.

It is another object of the present invention to provide methods for the storage and administration of API's utilizing inclusion of the API's within single crystals.

Other objects, features, and advantages of the present invention will be apparent to those skilled in the art from the following description and claims.

DESCRIPTION OF THE PREFERRED EMBODIMENT

Figure 1:
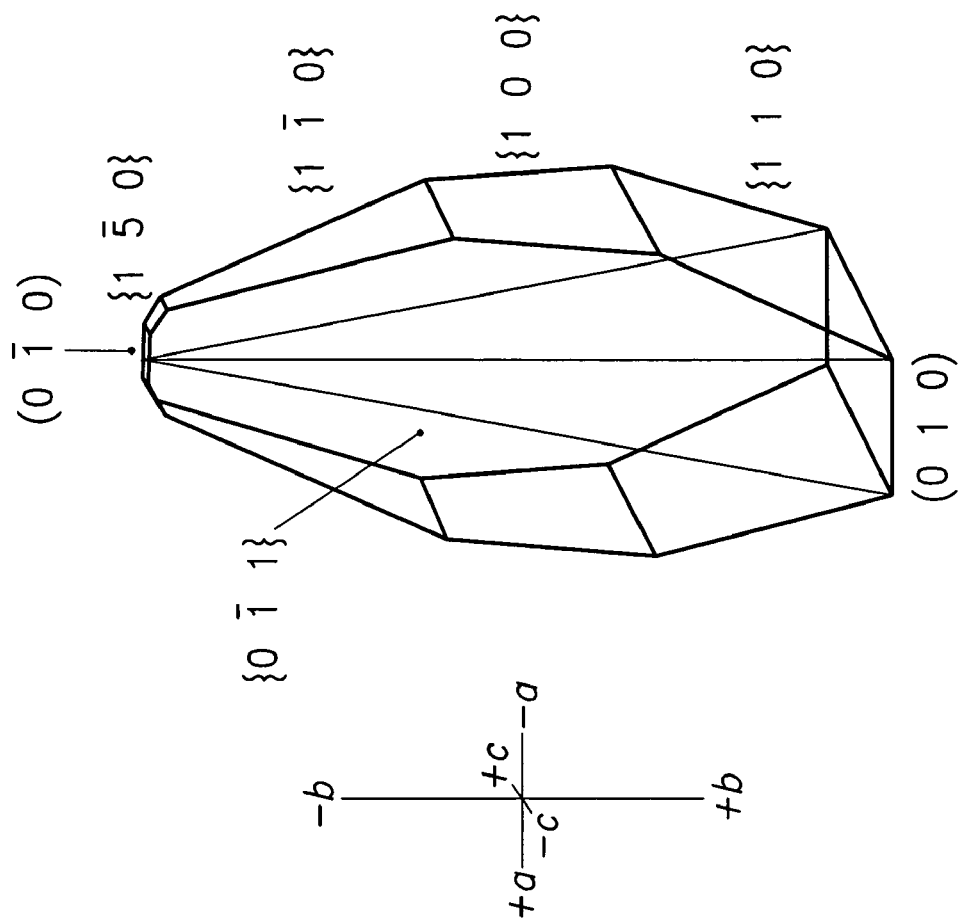
FIG. 1 is a photomicrograph illustrating fluorescence of a single crystal of green fluorescent protein in $\alpha$-lactose monohydrate (1.8 (h)×0.8 (w)×0.5 (d) $mm^3$) with an idealized representation of habit. The sides of the crystal in the photomicrograph are bright due to internal reflection.
Figure 1:
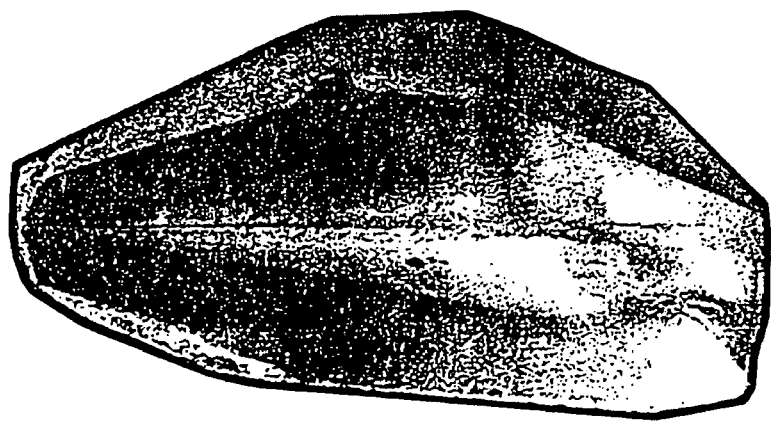

For the purposes of promoting an understanding of the present invention, reference will now be made to the embodiments described hereafter. It will nevertheless be understood that no limitation of the scope of the invention is thereby intended, such modifications and applications of the principles of the invention as described herein being contemplated as would normally occur to one skilled in the art to which the invention relates.

The present invention utilizes single-crystal matrix inclusion of active pharmaceutical ingredients ("API's") to achieve advantageous storage and delivery of the API's. This invention has application to a wide range of API's to provide enhanced stability and/or delivery of the active pharmaceutical ingredients. For some applications, such as for many biopharmaceuticals, the invention is particularly advantageous in providing greater stability over time and in providing alternative delivery and sustained release formulations to patients.

The small molecule host crystals comprise a crystal lattice component which includes the API's in an oriented, growth-sector specific manner. The crystals and included API's are prepared to be pharmaceutically acceptable and pure, thereby being useful for administration to patients to be treated with the API's. As used herein, the term "pharmaceutically-acceptable" refers to sufficient quality to meet regulatory and compendial requirements for administration to humans and/or animals. The crystals provide a regular, predictable inclusion of the guest active pharmaceutical ingredient, and the crystals can consequently be used for obtaining a predetermined amount of the active pharmaceutical ingredient for delivery to a patient. In one aspect, the host crystal gradually dissolves upon contact with body tissue or fluids, and is therefore useful as a system for delivery of the active pharmaceutical ingredient into the body. Alternatively, the crystals and included active pharmaceutical ingredient may be reconstituted into a solution for administration to a patient.

The active pharmaceutical ingredient molecules are generally isolated from one another and are insulated from the environment by the host crystal. This leads to reduce susceptibility of the API to degradation, and therefore enhanced stability and shelf-life. Also, the use of appropriate host crystal compounds, or selected dosage forms, permits the design of quick, delayed, or sustained-release formulations for delivery of the active pharmaceutical ingredient. Sustained-release formulations are particularly advantageous for treatment of chronic conditions as they provide a consistent amount of drug delivery over a long period of time to improve ease of use and patient compliance in administering the API.

The crystal preferentially incorporate the active pharmaceutical ingredient on certain faces, thereby providing a growth-sector specific inclusion and orientation to the API's. As used herein, the term "growth-sector specific inclusion and orientation," and equivalent terminology, refers to the fact that the API molecules are included primarily at certain faces of the crystal matrix. The growth-sector specific inclusion and orientation can be determined by one skilled in the art, as demonstrated in the examples herein, by fluorescence microscopy and anisotropy measurements, single crystal desorption mass spectrometry, and autoradiography of $^{14}$C-labeled material. In one embodiment, at least about 0.001% (on weight/weight (w/w) basis) of the pharmaceutical is included within specific faces of the crystal matrix, and in another embodiment at least about 0.1% (w/w) and up to about 10%. The crystal parameters, including the particular crystal lattice component for a given API, the concentration of API, the use of crystal adjuvants, and the crystallization conditions, are selected to achieve the growth-sector specific inclusion and orientation of the API within the crystals.

The method of the present invention broadly involves the including of the active pharmaceutical ingredient into the single crystal matrix formed from a pharmaceutically-acceptable crystal lattice component. As used herein, the term "included" in the crystals refers to the active pharmaceutical ingredient being chemically adsorbed within the crystal lattice as the crystal is formed. This inclusion of the active pharmaceutical ingredient molecules is distinguished from crystallization of the API molecules with one another, and from simple and random entrapment of the API molecules by the formed crystal. The crystal product of the present invention is ordered, in contrast to the amorphous material produced by other approaches. The API is incorporated in the crystal in relation to its degree of affinity for the crystal lattice molecules. The crystal lattice component is therefore selected to be both chemically and physically compatible with the API such that the API is received by the crystal during formation, and remains stable and efficacious while within the crystal and upon release therefrom.

In a typical approach, the including of the active pharmaceutical ingredient involves combining the crystal lattice component, the active pharmaceutical ingredient and a pharmaceutically-acceptable adjuvant in a liquid state. The crystal lattice component is then crystallized under pharmaceutically-acceptable conditions to form the inventive crystals. For example, one method uses spiking of the API into a saturated or supersaturated solution of the crystal lattice component in a suitable organic and/or aqueous solvent system. Alternatively, the saturated or supersaturated solution of the crystal lattice component may be spiked into the API solution. Other components may also be added to the solution, including compounds which facilitate or modify crystal growth or which are desired for incorporation in the final formulation. The solution may be seeded using any of a variety of conventional techniques.

In one approach, the solution is allowed to evaporate and/or equilibrate to cooler conditions for growth of the crystals. The crystals are then grown as the solvent is slowly evaporated away and/or the solution is cooled, with the evaporation and temperature gradient conditions being selected dependent on such factors as the solvent system and the desired crystal size. The crystals containing the active pharmaceutical ingredient are harvested from the remaining solution and are preferably washed to remove surface contamination. This procedure yields crystals which include the active pharmaceutical ingredient at a predictable concentration and facial orientation.

In accordance with the present invention, crystals are grown under pharmaceutically-acceptable conditions. As used herein, the term "pharmaceutically-acceptable conditions" refers to the use of crystal and API compounds which are pharmaceutically-pure, and for which such pharmaceutical purity is maintained in the final crystals. The crystal and API compounds are pharmaceutically pure, or have pharmaceutical purity, if they are of sufficient purity to be suitable for administration under applicable FDA or other administrative regulations regarding purity. The term pharmaceutically-acceptable conditions further refers to the user of crystallization conditions through which the API compounds retain pharmaceutical efficacy in the final crystals and upon subsequent administration to patients.

The present invention readily allows the inclusion of API's by affinity with the small host molecules in the growing crystal lattice. This overcomes many of the limitations associated with approaches. The processing involved with preparing the present crystals does not expose the API's to harsh conditions, thereby substantially reducing or avoiding the possible degradation or disruption of the structural aspects of the API which could occur with prior art techniques. The inventive crystals have an added advantage in that they do not interfere with normal analytical methodologies used for characterizing the pharmaceutical product. The small host molecules can be easily separated on the basis of molecular size, which is not the case for prior art techniques which uses polymers that interfere with analytical methodologies.

The API molecules are incorporated into the host crystals typically at rates of at least about 0.001% (w/w), preferably at least about 0.1%, and more preferably about 1% to about 10% (w/w). Alternatively, the API molecules are included at rates of at least about 0.01%, and as much as at least about 1% (w/w). The limited molar concentration of the active pharmaceutical ingredient in the host crystals means that the active pharmaceutical ingredient molecules are generally isolated from one another in the crystals. Isolation of the API molecules is particularly advantageous for those molecules, such as certain biopharmaceuticals, which could otherwise react with one another (e.g., by polymerization) or the surrounding environment. The degree of isolation can be verified by those skilled in the art using atomic force microscopy or reaction fluorescence energy techniques. The present invention has a particular application to guest-host systems in which the guest API molecules are reactive with one another, but in which these molecules are sufficiently isolated from one another in the crystals as to substantially prevent such interaction. Consequently, the invention provides containment of the API molecules in the solid state crystals and provides for the API to be comformationally stable.

The method preferably involves preparing a mixture of crystals of substantially uniform size. This may include processing of the harvested crystals, such as by grinding or milling, to reduce the crystals to a substantially uniform size. Greater uniformity can be achieved by sorting the processed crystals, such as by sieving. A preferred method further includes obtaining crystals which have a substantially uniform concentration of pharmaceuticals, for example, about 1% (w/w) of pharmaceuticals, that do not vary between crystals by more than 10 percent.

The method of the present invention may further include formulating the crystals into pharmaceutical preparations. For example, the collected crystals may optionally be coated with a suitable composition. Coated or uncoated crystals may be blended with one or more pharmaceutically-acceptable adjuvants, such as excipients, diluents, carriers or mixtures thereof. The blended crystals and adjuvant(s) are then formulated into pharmaceutical delivery units. In one embodiment, each unit includes a predetermined amount of the pharmaceutical. Alternatively, the crystals are combined in a delivery unit intended to deliver multiple or sustained dosing of the API over a period of time, such as by subcutaneous implantation of the delivery unit. A further aspect of the method of the present invention involves reconstituting the crystals to liquid form. In accordance with this method, the harvested crystals are dissolved in a suitable diluent for the crystal lattice component. The dissolution of the crystals releases the API from the crystals. The resulting solution may include other adjuvants, such as excipients, diluents or carriers, and the mixture is formulated under conventional procedures to desired delivery forms. In a particular aspect of the present invention, the crystals are used to store the pharmaceutical for a period of times, such as at least one month, or at least one year, and the crystals are subsequently dissolved to use the active pharmaceutical ingredient.

The present invention involves the use of any of a wide variety of pharmaceutically-acceptable host crystal systems that can incorporate API's in a growing crystal lattice. The crystal lattice component is selected to be compatible with the guest API, and to be suited to the use of the resulting formulation for storage and administration. Selection of the crystal lattice component will involve consideration of such factors as affinity for the API, crystal size distribution and morphology, and desired pharmaceutical concentration and delivery rate, as well as other factors well known in the art of pharmaceutical delivery systems. The crystal systems must consistently incorporate the guest active pharmaceutical ingredient in terms of concentration and placement within the crystal lattice. The crystals also must grow under conditions which will not degrade or otherwise adversely effect the viability of the active pharmaceutical ingredient.

Preferred host crystal materials are those that have a high affinity for the included API. It appears that the oriented inclusion of the API's is related to the affinity between the crystal lattice component and the API. The affinity between these materials is therefore important in obtaining the desired inclusion of the API's, and also permits control of the inclusion based upon this affinity. For example, the concentration of the pharmaceutical in a crystal can be controlled by selecting the host component to have an affinity for the API which yields the desired inclusion rate. Also, mixtures of host materials, or of host materials and other excipients, can be used to provide an affinity yielding the desired inclusion level. In one aspect of the present invention, the API's are incorporated at levels of at least about 0.001% (w/w of guest:host), more preferably at least about 0.1% (w/w).

The preferred host crystal materials will also be very stable and readily crystallizable, and will maintain their "order" or crystal morphology when including a guest molecule, particularly large biomolecules. The use of particular host crystal components will also depend on such factors as how small or large the crystals can be produced and how readily they dissolve. For various routes of administration, it is desirable to have very small crystals (e.g., pulmonary), moderately sized crystals (e.g., injectable), or very large crystals (e.g., implantation and long term payout). The useful crystal sizes will therefore vary accordingly, ranging from submicron to millimeter sizes. In one aspect of the present invention the preferred crystals are in the order of 5–100 microns in size.

The useful host crystal systems are therefore diverse, and include various small molecule crystal systems which meet the desired criteria. Examples of pharmaceutically-acceptable crystal lattice components include sugars, polyhydroxy alcohols, single and polyamino acids, vitamins, salts, metals, preservatives, aromatic compounds especially aromatic acids, purified natural products, and polymers. Preferred crystal lattice components include, for example, sucrose, lactose, trehalose, maltose, galactose, sorbose, mannitol, lactitol, sorbitol, glycine, alanine, lysine, arginine, ascorbic acid, nicotinamide, thiamine, adenine, pyridoxine hydrochloride, caffeic acid, vanillic acid, ferulic acid, benzoate, sorbate, methyl paraben, sodium ascorbate, sodium saccharin, and potassium citrate. Also, compatible mixtures of these materials are also useful, and can be selected to obtain the desired rate of inclusion of the pharmaceutical, or to achieve desired characteristics, such as dissolution rate and pharmacokinetic profile, for the product crystals.

The crystal lattice components are selected to achieve the desired pharmacokinetics for the final crystals. As pertains to the present invention, the term "pharmacokinetics" is used to refer to the profile of the delivery of active pharmaceutical ingredient from the crystals into the circulatory system. This will depend primarily on the concentration of the active pharmaceutical ingredient in the crystals, as well as parameters of the active pharmaceutical ingredient itself. While given crystal lattice components will have associated inclusion and dissolution characteristics, these can be modified by including other crystal lattice components, other API's, or a variety of excipients. Thus, single crystals having two different, co-crystallied lattice components will typically be characterized by pharmacokinetic profiles different from crystals prepared with either of the crystal lattice components alone. Similarly, including excipients or other API's will provide altered rates of inclusion or dissolution for the resulting crystals, providing an associated modification in the pharmacokinetic profile for the resulting crystals.

In a related aspect, the present invention involves the use of mixtures of crystals having different pharmacokinetics in order to achieve desired payout profiles. For example, a pharmaceutical product can be obtained by combining two different types of crystals, one type of crystal using a first crystal lattice component characterized by a first pharmacokinetic profile, and the second type of crystal using a second crystal lattice component characterized by a second pharmacokinetic profile. The mixture of crystals will give a payout of API that is different from either of the individual payouts for the two crystal types.

The included API's are similarly diverse, limited simply by the requirements of compatibility with the host crystal and the crystal growth conditions. The active pharmaceutical ingredient cannot be unacceptably degraded or otherwise adversely affected by the conditions under which the crystals are formed. Also, the active pharmaceutical ingredient should remain stable for an extended period of time while included within the host crystal, and pharmaceutically efficacious upon release from the crystal.

Given the foregoing criteria, examples of API's useful in accordance with the present include: antibiotics (such as dirithryomycin, loracarbef, tilmicosin, vancomycin, tylosin, monensin), fluoxetine, raloxifene, olanzapine, and nizatidine. A more complete list of API's useful in accordance with the present invention would include those identified in the following Table A.

TABLE A

Marketed Recombinant Protein Products

Tissue Plasminogen Activator, T-PA

Product name: Activase (Generic name: Altepase)
Produced by: Genentech
Indication: Human use, Acute myocardial infarction
Date of approval: November 87, Patent expires on December 2000.
Formulation: Intravenous injection. Lyophilized powder which is reconstituted with sterile water (supplied) to 1 mg/mL and results in a final pH of 7.3. Can not be reconstituted with preserved water due to precipitation. The 1 mg/mL solution can be diluted 1:1 with 0.9% NaCl or D5W and help for 8 hours at room temperature. TPA is incapable with preservatives.

| Ingredients | 100 mg vial | 50 mg vial | 20 mg vial |
| --- | --- | --- | --- |
| T-PA | 100 mg | 50 mg | 20 mg |
| L-Arginine | 3.5 g | 1.7 g | 0.7 g |
| Phosphoric acid | 1 g | 0.5 g | 0.2 g |
| Polysorbate 80 | <11 mg | <4 mg | <1.6 mg |
| Vacuum | No | Yes | Yes |

Expression System: Mammalian cell line (Chinese Hamster Ovary cells)
Refolding Conditions:
Structure: Glycoprotein of 527 amino acids, sequence from human melanoma cell line, activity of 580,000 IU/mg.
Additional Information: Sales > $100 million. Cost of therapy $2,750 (100 mg).

TABLE A-continued

Interferon Gamma-1b

Product name: Actimmune
Produced by: Genentech
Indication: Human use, chronic granulomatous disease
Date of approval: December 1990
Formulation: Single dose solution formulation (0.5 mL), subcutaneous injection. Each 0.5 mL contains 100 μg interferon gamma-1b, 20 mg mannitol, 0.36 mg sodium succinate, 0.05 mg polysorbate-20 in sterile water.
Expression System: *E. coli*
Refolding Conditions:
Post-Transitional Modifications:
Structure: Single chain; Human sequence, 140 amino acids, 16,465 molecular weight, non-covalent dimeric form in solution, activity or 30 million units/mg.
Additional Information: 14% injection site irritation vs. 2% in placebo. Cost $140 for 50 μg.
Interferon alfa-n3 (natural source, not recombinant)

Product name: Alferon N
Produced by: Interferon Science (New Brunswick, NJ)
Indication: Human use, Genital Warts
Date of approval: June 90
Formulation: Preserved solution formulation (each mL contains 5 million IU of interferon alfa-n3 in phosphate buffered saline containing 3.3 mg phenol and 1 mg human albumin). Injected intralesional twice weekly for up to 8 weeks (50 μL injected into each wart, 500 μL total dose per treatment).
Expression System: Natural source - human leukocytes which are exposed to an avian virus in order to produce interferon.
Refolding Conditions: None
Structure: Approximately 166 amino acids with a molecular weight ranging from 16 to 27 kDa, specific activity of 20,000 IU/m° or greater.
Additional Information: Cost $142 per mL.
Beta Interferon 1a Product name: Avonex
Produced by: Biogen (Cambridge, MA)
Indication: Human use, Multiple Sclerosis
Date of approval: May 95
Formulation: Lyophilized powder (stored refrigerated or at 25° C. for < 30 days) which is reconstituted with sterile water (supplied, 1.1 mL) to 30 μg/mL beta interferon 1a, 15 mg/mL human albumin, 5.8 mg/ml NaCl, 5.7 mg/ml dibasic Na phosphate, 1.2 mg/ml monobasic sodium phosphate, and has a pH of approximately 7.3 (recon solution is stable for 6 hours at refrigerated temperatures). Weekly intramuscular injection by patient or doctor (dosed for 1–2 years in clinical trials).
Expression System: Mammalian cells (Chinese Hamster Ovary cells)
Refolding Conditions:
Structure: Glycoprotein (single N-linked complex carbohydrate), 166 amino acids with a predicted molecular weight of 22,500 daltons, human sequence, has a specific activity of 200 million units per mg protein.
Additional Information: Cost $180 per vial (33 μg)
Interferon beta-1b Product name: Betaseron
Produced by: Berlex Laboratories (Wayne, NJ and Chiron, Emeryville, CA)
Indication: Human use, Multiple Sclerosis
Date of approval: July 93.
Formulation: Lyophilized product (stored refrigerated) which is reconstituted with 0.54% NaCl (supplied) to 0.25 mg/mL interferon beta-1b, 12.5 mg/mL human albumin, 12.5 mg/ml dextrose, and has a pH of approximately 7.3 (recon solution is stable for 3 hours). Injected subcutaneously every other day (chronic use).
Expression System: *E. coli*
Refolding Conditions:
Structure: 165 amino acids with an approximate molecular weight of 18,500 daltons, human sequence but with a serine or cysteine substitution at residue 17. Recombinant form does not contain the carbohydrate moiety found in the natural material. Has a specific activity of 32 million units per mg protein.
Additional Information: Sales > $500 million. Cost of therapy is $13,140 (based on 0.25 mg/injection, dose every other day for 1 year; equals 46 mg protein).
Interferon alfa-2b Product name: Intron A
Produced by: Schering-Plough (Madison, NJ)
Indication: Human use, Hairy cell leukemia, genital warts, Hepatitis, Melanoma, Kaposi's sarcoma
Date of approval: June 86
Formulation: Comes in a lyophilized and a solution formulation. The lyophilized formulations when reconstituted with 0.9% benzyl alcohol (supplied) contains either 0.015, 0.025, 0.05, 0.90, or 0.125 mg/ml. Interferon alfa-2b, 20 mg/ml glycine, 2.3 mg/ml sodium phosphate dibasic, 0.55 mg/ml sodium phosphate monobasic, and 1 mg/ml human albumin. The solution formulations contain either 0.05, 0.114, or 0.125 mg/mL Interferon alfa-2b, 20 mg/ml glycine, 2.3 mg/ml sodium phosphate dibasic, 0.55 mg/ml sodium phosphate monobasic, 1 mg/ml human albumin, 1.2 mg/mL methylparaben, and 0.12 mg/ml propylparaben. These formulations be injected intramuscular, subcutaneous, or intralesional. All formulations and reconstituted products are stored at refrigerated temperatures.
Expression System: *E. coil*

TABLE A-continued

Refolding Conditions:
Structure: Water soluble protein a molecular weight of 19,271 daltons. The Interferon alfa-2b gene is derived from human leukocytes.
Additional Information: Sales > $500 Million. Cost of therapy is $16,445 (5 mlllion units every day for 1 year, this is equal to 9 mg protein). Specific activity is 200 million units per mg protein Interferon alfa-2a Product name: Roferon-A
Produced by: Hoffmann-La Roche (Nutley, NJ)
Indication: Human use, Hairy cell leukemia, Kaposi's sarcoma, myelogenous leukemia
Date of approval: June 1986
Formulation: Multi-use and lyophilized formulation indented for intramuscular or subcutaneous administration. Multi-use formulation contains either 0.015, 0.045, 0.090, 0.18 mg/mL Interferon alfa-2a, 9 mg/ml NaCl, 5 mg/ml human albumin, and 3 mg/ml phenol. The lyophilized formulation reconstituted with 3 mL of supplied diluent (6 mg/ml NaCl, 3.3 mg/ml phenol) consists of 0.03 mg/ml Interferon alfa-2a, 9 mg/ml NaCl, 1.67 mg/ml human albumin, and 3.3 mg/ml phenol.
Expression System: *E. coli* (tetracycline promoter).
Refolding Conditions:
Structure: Protein of 165 amino acids having a molecular weight of 19,000 daltons
Additional Information: Cost of therapy is $59,200 (28 mg protein over 1 year). Specific activity is 200 million international units per mg protein.

Human Growth Hormone (Somatropin)

Product name: BioTropin
Produced by: Bio-Technology General (Iselin, NJ)
Indication: Human use, Growth Deficiency
Date of approval: May 95
Formulation:
Expression System:
Refolding Conditions:
Post-Transitional Modifications:
Structure:
Additional Information:

Human Growth Hormone (Somatropin)

Product name: Genotropin
Produced by: Pharmacia and Upjohn (Kalamazoo, MI)
Indication: Human use, Growth Deficiency
Date of approval: August 95
Formulation:
Expression System:
Refolding Conditions:
Structure:
Additional Information:

Human Growth Hormone (Somatropin)

Product name: Humatrope
Produced by: Eli Lilly (Indianapolis, IN)
Indication: Human use, Growth Deficiency
Date of approval: March 87
Formulation: Lyophilized product which is reconstituted with sterile water containing 0.3% m-cresol, 1.7% glycerin (supplied) to 2 mg/mL hGH and has a final pH of approximately 7.5, subcutaneous or intramuscular administration. Each 5 mg lyophilized vial contains 5 mg hGH, 25 mg mannitol, 1.13 mg dibasic sodium phosphate, and 5 mg glycine.
Expression System: *E. coli*.
Refolding Conditions:
Structure: 191 amino acids, molecular weight of 22,125 daltons, sequence is identical to human pituitary-derived material.
Additional Information: Cost $210 per 5 mg hGH.

Human Growth Hormone (Somatropin)

Product name: Norditropin
Produced by: Novo Nordisk (Princeton, NJ)
Indication: Human use, Growth Deficiency
Date of approval: July 91
Formulation:
Expression System:
Refolding Conditions:
Post-Transitional M difications:
Structure:
Additional Information:

Human Growth Hormone (Somatropin)

Product name: Nutropin and Nutropin AQ
Produced by: Genentech
Indication: Human use, Growth Deficiency
Date of approval: March 1994
Formulation: Lyophilized product which is reconstituted with bacteriostatic water (0.9% benzyl alcohol, supplied) to 5 mg/mL hGH and has a final pH of approximately 7.4, subcutaneous or intramuscular

TABLE A-continued administration. Each 5 mg lyophilized vial contains 5 mg hGH, 45 mg mannitol, 1.7 mg sodium phosphates (0.4 mg monobasic and 1.3 mg dibasic), and 1.7 mg glycine.
Expression System: *E. coli*, expressed with a leading secretion signal precursor which directs the protein to the plasma membrane of the cell where the sequence is removed and the native protein is secreted into the periplasm so that the protein if folded appropriately as it is synthesized
Refolding Conditions: None, expressed folded in *E. coli*.
Structure: 191 amino acids, molecular weight of 22,125 daltons, sequence is identical to human pituitary-derived material.
Additional Information: Cost $420 per 10 mg hGH.
β-Glucocerebrosidase (imiglucerase)
(β-D-glucosyl-N-acylsphingosine glucohydrolase, E.C.3.2.1.45)

Product name: Cerezyme
Produced by: Genzyme (Cambridge, MA)
Indication: Human use, Gaucher's disease
Date of approval: May 94
Formulation: Lyophilized product (212 units glucocerebrosidase, 155 mg mannitol, 70 mg sodium citrate, and 0.53 mg polysorbate-80; stored refrigerated) is reconstituted with 5.1 mL of sterile water, final pH is approximately 6.1. The reconstituted material is combined with 100 to 200 mL of 0.9% NaCl and administered intravenously.
Expression System: Mammalian cell culture (Chinese Hamster Ovary cells)
Refolding Conditions:
Structure: Monomeric glycoprotein of 497 amino acids, containing 4 N-linked glycosylation sites, molecular weight is 60,430 daltons. Recombinant protein differs from human placental glucocerebrosidase by a arginine substituted for histidine at position 495 and the glycosylation sites have been modified to terminate in mannose sugars (which are specifically recognized by endocytic carbohydrate receptors on macrophages, the cells that accumulate lipid in Gaucher disease).
Additional Information: Orphan Drug, sales > $100 million, Cost of therapy is $351,130 (1 year).
Hepatitis B Surface Antigen Product name: Engerix-B
Produced by: SmithKline Beechman (Philadelphia, PA)
Indication: Human use, Hepatitis B
Date of approval: September 89
Formulation: Suspension (20 μg/mL hepatitis B surface antigen adsorbed onto 0.5 mg aluminum, 1:20,000 thimerosal, 9 mg/ml NaCl, 1.7 mg/ml sodium phosphates). Intramuscular administration.
Expression System: A portion of the hepatitis B virus gene, coding for hepatitis B surface antigen, in cloned into yeast (*Saccharomyces cerevisiae*)
Refolding Conditions:
Post-Transitional Modifications:
Structure:
Additional Information: Formulation contains no more than 5% yeast proteins.
Hepatitis B Surface Antigen Product name: Recombivax HB
Produced by: Merck (Whithouse Station, NJ)
Indication: Human use, Hepatitis B prevention
Date of approval: July 1986
Formulation: Suspension (10 μg/ml hepatitis B surface antigen adsorbed onto 0.5 mg aluminum, 1:20,000 thimerosal). Intramuscular administration.
Expression System: A portion of the hepatitis B virus gene, coding for hepatitis B surface antigen, in cloned into yeast (*Sacccharomyces cerevisiae*)
Refolding Conditions:
Structure:
Additional Information: Formulation contains no more than 1% yeast proteins.
Erythropoietin (rEPO)

Product name: Epogen or Epoetin alfa (Also sold under the name Procrit by Ortho Biotech but manufactured by Amgen)
Produced by: Amgen (Thousand Oaks, CA)
Indication: Human use, Anemia
Date of approval: June 89, Patent expires in 2004 (December).
Formulation: Two solution formulations, single dose and multi-dose. Single-dose is preservative free and each mL contains 2000, 3000, 4000, or 10000 units Epogen, 2.5 mg human albumin, 5.8 mg sodium citrate, 5.8 mg NaCl, and 0.06 mg citric acid in water for injection, pH 6.9 +/− 0.3. The preserved multi-dose product contains 10,000 units Epogen, 2.5 mg human albumin, 1.3 mg sodium citrate, 8.2 mg sodium chloride, 0.11 mg citric acid and 1% benzyl alcohol per mL of solution, pH is 6.1 +/− 0.3. Both solutions are stored refrigerated.
Expression System: Mammalian cell
Refolding Conditions:
Structure: Glycoprotein of 165 amino acids having a molecular weight of 30,400 daltons, sequence identical to that of the human protein.
Additional Information: Sales > $500 million, Cost $120 for 10,000 units.
Human Insulin Product name: Humulin
Produced by: Eli Lilly (Indianapolis, IN)
Indication: Human use, Diabetes
Date of approval: October 82

TABLE A-continued

Formulation:
Expression System: *E. Coli*
Refolding Conditions:
Structure:
Additional Information: Sales > $500 Million.
Human Insulin Product name: Novolin
Produced by: Novo Nordisk (Princeton, NJ)
Indication: Human use, Diabetes
Date of approval: July 91
Formulation:
Expression System:
Refolding Conditions:
Post-Transitional Modifications:
Structure:
Additional Information:
LysPro Human Insulin Product name: Humulog
Produced by: Eli Lilly (Indianapolis, IN)
Indication: Human use, Diabetes
Date of approval: June 1996
Formulation:
Expression System:
Refolding Conditions:
Post-Transitional Modifications:
Structure:
Additional Information:
GM-CSF (Granulocyte Macrophage-Colony Stimulating Factor)

Product name: Leukine
Produced by: Immunex (Seattle, WA)
Indication: Human use, Bone marrow transplantation, Hodgkin's Disease, Leukemia
Date of approval: March 91
Formulation: Lyophilized solution which is reconstituted with sterile water (stored at refrigerated temperatures for < 6 hours) or 0.9% benzyl alcohol (can be stored for < 20 days at refrigerated temperatures) and administered intravenous. After reconstitution, the lyophilized single use product contains either 0.25 mg/mL or 0.50 mg/mL GM-CSF, 40 mg/ml mannitol, 10 mg/ml sucrose, and 1.2 mg/ml tromethamine (final pH is 7.4 +/− 0.3). The reconstituted solution is then diluted into a 0.9% NaCl bag for IV administration (note if final GM-CSF is below 0.01 mg/mL add human albumin to 0.1% to prevent adsorption to the IV bag.
Expression System: Yeast (*S. Cerevisiae*)
Refolding Conditions: None, expressed folded.
Structure: Glycoprotein of 127 amino acids characterized by 3 primary molecular species having molecular masses of 19,500, 16800, and 15500 daltons. The primary sequence differs from natural human GM-CSF by a substitution of leucine at position 23, and the carbohydrate moiety may be different from native.
Additional Information: Specific activity is $5 \times 10^7$ colony forming units per mg protein. Sargramostim is the proper name for yeast-derived recombinant GM-CSF. Cost for a 0.5 mg GM-CSF vial is $178.
G-CSF (Granulocyte Colony Stimulating Factor)

Product name: Neupogen
Produced by: Amgen (Thousand Oaks, CA)
Indication: Human use, Neutropenia, bone marrow transplantation, anemia
Date of approval: February 91
Formulation: Single-use solution formulation containing 0.3 mg/mL G-CSF, 10 mM sodium acetate, 5% mannitol, and 0.004% Tween-80 at a pH of 4. The product is to be stored at refrigerated temperatures and no more than 24 hours at room temperature. If required, Neupogen can be diluted with D5W (no not dilute with saline at any time; product may precipitate), at concentrations below 5 to 15 μg/mL, add human albumin to 2 mg/mL to prevent adsorption to IV bag.
Expression System: *E. coli*.
Refolding Conditions:
Structure: A 175 amino acid protein with a molecular weight of 18,800 daltons. The protein has an amino acid sequence identical to the human protein except for an additional N-terminal methionine (necessary for expression in *E. coli*). The human protein is glycosylated but the recombinant Neupogen is not.
Additional Information: Sales > $500 million. Filgrastim is the name give to recombinant methionyl human G-CSF. Cost of therapy (lung cancer) is $2,130 (4.2 mg protein over 14 days). Specific activity is 30 million units per mg protein.
Satumomab Pendetide Product name: OncoScint CR/OV
Produced by: Cytogen (Princeton, NJ)
Indication: Human use, Colorectal and ovarian cancers
Date of approval: December 92
Formulation:
Expression System:
Refolding Conditions:
Post-Transitional Modifications:

TABLE A-continued

Structure:
Additional Information:
<u>Interleukin-2</u>

Product name: Proleukin (generic name: Aldesieukin)
Produced by: Chiron (Emeryville, CA)
Indication: Human use, Renal cell carcinoma
Date of approval: May 1992
Formulation: Single-use lyophilized formulation which is reconstituted with 1.2 mL sterile water and administered intravenously. Each reconstituted product contains 1.1 mg/mL Proleukin, 50 mg/ml mannitol, and 0.18 mg/ml dibasic sodium phosphate (pH is 7.5 +/− 0.3). Lyophilized product is stored at refrigerated temperatures, reconstituted product is stable up to 48 hours at refrigerated to room temperatures, but should be stored in refrigerator due to lack of preservatives. Addition of preservatives results in increased aggregation, addition of human albumin alters pharmacology.
Expression System: *E. coli* (tetracycline promoter).
Refolding Conditions:
Structure: Proleukin has a molecular weight of 15,300 daltons and differs from the natural human protein (is not glycosylated, the N-terminal alanine is removed, and has a serine substituted for the free cysteine at position 125)
Additional Information: Specfic activity is 18 million international units per 1.1 mg protein. Cost is $395 per 1.3 mg protein.
<u>Somatrem</u>

Product name: Protropin
Produced by: Genentech (S. San Francisco, CA)
Indication: Human use, Growth deficiency
Date of approval: October 1985, patent expired on October 1992.
Formulation: Lyophilized formulation which is reconstituted with 0.9% benzyl alcohol (supplied) and administered intramuscular or subcutaneous. The lyophilized vial contains 5 mg Somatrem, 40 mg mannitol and 1.7 mg sodium phosphates (0.1 mg sodium phosphate monobasic and 1.6 mg sodium phosphate dibasic) and is reconstituted with 1 to 5 mL of 0.9% benzyl alcohol. The lyophilized product is stored at refrigerated temperature, the reconstituted product is good for 14 days at refrigerated temperatures.
Expression System: *E. coli*.
Refolding Conditions:
Structure: Contains 192 amino acids with molecular weight of 22,000 daltons. Identical to human sequence but contains an extra methionine at the N-terminus.
Additional Information: Sales > $100 million. Cost of therapy is $13,110 (1 year, 313 mg protein)
<u>DNase (deoxyribonuclease I)</u>

Product name: Pulmozyme
Produced by: Genentech (S. San Francisco, CA)
Indication: Human use, Cystic fibrosis
Date of approval: December 1993
Formulation: Inhalation solution (aerosol mist produced by a compressed air driven nebulizer system). Comes in a single-use 2.5 mL ampule containing 1.0 mg/mL DNase, 0.15 mg/mL calcium chloride dihydrate, and 8.77 mg/ml sodium chloride, at a pH of 6.3. The solution is stored at refrigerated temperatures and should not be exposed to light.
Expression System: Mammalian cells (Chinese hamster Ovary cells)
Refolding Conditions:
Structure: Glycoprotein of 260 amino acids having a molecular weight of 37,000 daltons. The primary sequence is identical to that of the native human enzyme.
Additional Information: Sales > $100 Million. Cost is $32 for 2.5 mg of protein (1 ampule)
<u>M-CSF (Macrophage-Colony Stimulating Factor)</u>

Product name: Leucomax (generic name: Molgramostim)
Produced by:
Indication: Human use,
Date of approval: FDA unapproved
Formulation:
Expression System:
Refolding Conditions:
Post-Transitional Modifications:
Structure:
Additional Information:
<u>Epoetin Beta (Erythropoietin)</u>

Product name: Marogen
Produced by:
Indication: Human use,
Date of approval:
Formulation:
Expression System:
Refolding Conditions:
Post-Transitional Modifications:
Structure:
Additional Information:

TABLE A-continued

Polyribonucleotide

Product name: Ampligen
Produced by:
Indication: Human use,
Date of approval: FDA Unapproved
Formulation:
Expression System:
Refolding Conditions:
Post-Transitional Modifications:
Structure:
Additional Information:
Human Serum Albumin Product name:
Produced by:
Indication: Human use,
Date of approval:
Formulation:
Expression System:
Refolding Conditions:
Post-Transitional Modifications:
Structure:
Additional Information:
Septomonab?

Product name: Gentoxin
Produced by:
Indication: Human use,
Date of approval: Not FDA approved
Formulation:
Expression System:
Refolding Conditions:
Post-Transitional Modifications:
Structure:
Additional Information:
Protein Product name:
Produced by:
Indication: Human use,
Date of approval:
Formulation:
Expression System:
Refolding Conditions:
Post-Transitional Modifications:
Structure:
Additional Information:

APPROVED BIOTECHNOLOGY DRUGS AND VACCINES

| Product Name | Company | Product Category | Indication |
|---|---|---|---|
| Cornvax ™ Haemophilus b conjugate (meningococcal protein conjugate) and hepatitis b (recombinant) vaccine | Merck Whitehouse Station, NJ. | recombinant vaccine | vaccination of infants beginning at two months of age against both invasive Haemophilus influenzae type b diseases (Hib) and hepatitis B (October 1996) |
| Engerix-B ® hepatitis B vaccine (recombinant) | SmithKline Beecham Philadelphia, PA | recombinant vaccine | hepatitis B (September 1989) |
| EPOGEN ® Epoetin alfa (rEPO) | Amgen Thousand Oaks, CA | erythropoietin | treatment of anemia associated with chronic renal falure, including patients on dialysis and not on dialysis, and anemia in Retrovir ®-treated HIV-infected patients (June 1998); treatment of anemia caused by chemotherapy in patients with non-myeloid malignancies (April 1993); prevention of anemia associated with surgical blood loss, autologous blood donation adjuvant (December 1996) |
| PROCRIT ® Epoetin alfa (rEPO) | Ortho Biotech Raritan, NJ | erythropoietin | treatment of anemia associated with chronic renal failure, including patients on dialysis and not on dialysis, and anemia in Retrovi ®-treated HIV-infected patients (December 1990); treatment of anemia caused by chemotherapy in patients with non-myeloid malignancies (April 1993); prevention of anemia |

TABLE A-continued

| | | | |
|---|---|---|---|
| [PROCRIT was approved for marketing under Amgen's epoetin alfa PLA. Amgen manufactures the product for Ortho Biotech J Under an agreement bewteen the two companies, Amgen licensed to Ortho Pharmaceutical the U.S. rights to epoetin alfa for indications for human use excluding dialysis and diagnostics. | | | associated with surgical blood loss, autologous blood donation adjuvant (December 1996) |
| Genotropin ™ somatropin (rDNA origin) for injectiojn | Pharmacia & Upjohn Kalamazoo, MI | human growth hormone | short stature in children due to growth hormone deficiency (August 1995) |
| Gerel ® human growth hormone releasing factor | Serono Laboratories Norwell, MA | growth factor | evaluation of the ability of the somatotroph of the pituitary gland to secrete growth hormone (December 1990); pediatric growth hormone deficiency (October 1997) |
| Genal-F ® recombinant human follicle-stimulating hormone (r-FSH) | Serono Laboratories Norwell, MA | recombinant fertility hormone | female infertility (September 1997) |
| Humalog ™ insulin lispro | Eli Lilly Indianapolis, IN | recombinant insulin | diabetes (June 1996) |
| Humatrope ® somatropin (rDNA origin) for injection | Eli Lilly Indianapolis, IN | human growth hormone | human growth hormone deficiency in children (March 1987) |
| Humulin ® human insulin (recombinant DNA origin) | Eli Lilly Indianapolis, IN | recombinant insulin | diabetes (October 1982) |
| infergen ® interferon alfacon-1 | Amgen Thousand Oaks, CA | interferon | treatment of chronic hepatitis C viral infection (October 1997) |
| Intron ® A interferon alfa-2b (recombinant) | Schering-Plough Madison, NJ | interferon | hairy cell leukemia (June 1986); genital warts (June 1988); AIDS-related Kaposi's sarcoma (November 1988); hepatitis C (February 1991); hepatitis B (July 1992); malignant melanoma (December 1995); follicular lymphoma in conjunction with chemotherapy (November 1997) |
| KoGENate ® antihemophiliac factor (recombinant) | Bayer Corporation, Pharmaceutical Division West Haven, CT | clotting factor | treatment of hemophilia A (February 1993) |
| Leukine ™ sargramostim (GM-CSF) | Immunex Seattle, WA | colony stimulating factor | autologous bone marrow transplantation (March 1991); neutropenia resulting from chemotherapy in acute myelogenous leukemia (September 1995); allogeneic bone marrow transplantation (November 1995); peripheral blood progenitor cell mobilization and transplantation (December 1995) |
| MyoScint ® imiclromab pentetate | Centocor Malvern, PA | MAb | myocardial infarction imaging agent (July 1996) |
| Neumega ® oprelvekin | Genetics Institute Cambridge, MA | MAb | prevention of severe chemotherapy-induced thrombocytopenia (November 1997) |
| NEUPOGEN ® Filgrastim (rG-CSF) | Amgen Thousand Oaks, CA | colony stimulating factor | chemotherapy-induced neutropenia (February 1991); autologous or allogeneic bone marrow transplantation (June 1994); chronic severe neutropenia (December 1994); support peripheral blood progenitor cell transplantation (December 1995) |
| Norditropin ® somatropin (rDNA origin) for injection | Novo Nordisk Pharmaceuticals Princeton, NJ | human growth hormone | treatment of growth failure in children due to inadequate of growth hormone secretion (May 1995) |
| Novolin ® 70/30 70% NPH human insulin isophane suspension & 30% regular, human insulin | Novo Nordisk Pharmaceuticals Princeton, NJ | recombinant insulin | insulin-dependent diabetes mellitus (July 1991) |

TABLE A-continued

| | | | |
|---|---|---|---|
| injection (recombinant DNA origin) | | | |
| Novolin ® I. Lente ®, human insulin zinc suspension (recombinant DNA origin) | Novo Nordisk Pharmaceuticals Princeton, NJ | recombinant insulin | insulin-dependent diabetes mellitus (July 1991) |
| Novolin ® N NPH, human insulin isophane suspension (recombinant DNA origin) | Novo Nordisk Pharmaceuticals Princeton, NJ | recombinant insulin | insulin-dependent diabetes mellitus (July 1991) |
| Novolin ® R regular, human insulin injection (recombinant DNA origin) | Novo Nordisk Pharmaceuticals Princeton, NJ | recombinant insulin | insulin-dependent diabetes mellitus (July 1991) |
| Nutropin ® somatropin for injection | Genentech S. San Francisco, CA | human growth hormone | growth failure in children due to chronic renal insufficiency, growth hormone inadequacy in children (March 1994); Turner's syndrome (December 1996); growth hormone inadequacy in adults (December 1997) |
| Nutropin AQ ™ somatropin (liquid) | Genentech S. San Francisco, CA | human growth hormone | growth failure in children due to chronic renal insufficiency, growth hormone inadequacy in children (December 1995); Turner's syndrome (December 1996); growth hormone inadequacy in adults (December 1997) |
| OncoScint ™ CR/OV satumomab pendetide | CYTOGEN Princeton, NJ | MAb | detection, staging and follow-up of colorectal and ovarian cancers (December 1992) |
| ORTHOCLONE OKT ®3 muromonab-CD3 | Ortho Biotech Raritan, NJ | MAb | reversal of acute kidney transplant rejection (June 1986); reversal of heart and liver transplant rejection (June 1993) |
| Proleukin ® aldesleukin (interleukin-2) | Chiron Emeryville, CA | interleukin | renal cell carcinoma (May 1992); metastatic melanoma (January 1998) |
| ProstaScint ® capromab pentetate | CYTOGEN Princeton, NJ | MAb | detection, staging and follow-up of prostate adenocarcinoma (October 1996) |
| Protropin ® somatrem for injection | Genentech S. San Francisco, CA | human growth hormone | human growth hormone deficiency in children (October 1985) |
| Pulenozyme ® domase alpha, recombinant | Genentech S. San Francisco, CA | recombinant DNase | cystic fibrosis (December 1993); management of advanced cystic fibrosis (December 1996) |
| Recombinate ™ antihemophilic factor recombinant (rAHF) | Baxter Healthcare/ Hyland Division Glendale, CA Genetics Institute Cambridge, MA | clotting factor | hemophilia A (December 1992) |
| RECOMBIVAX HB ® hepatitis B vaccine (recombinant), MSD | Merck Whitehouse Station, NJ | recombinant vaccine | hepatitis B prevention (July 1986) |
| Refludan ™ lepirudin [rDNA] for injection | Hoechst Marion Roussel Kansas City, MO | recombinant anticoagulant | heparin-induced thrombocytopenia type II (March 1998) |
| Regranex ® becaplemin | Orthro-McNeil Pharmaceuticals Raritan, NJ | growth factor | lower extremity disbetic neuropathic ulcers (December 1997) |
| ReoPro ® abciximab | Centocor Malvern, PA Eli Lilly Indianapolis, IN | MAb | anti-platelet prevention of blood clots in the setting of high-risk percutaneous transluminal coronary angioplasty (December 1994); refractory unstable angina when percutaneous coronary unstable angina when (November 1997) |
| Retevase ™ reteplase | Boehringer Mannheim Gaithersburg, MD Centocor Malvern, PA | tissue plasminogen factor | treatment of acute myocardial infarction (October 1996) |
| Rituxan ® rituximab | Genentech S. San Francisco, CA IDEC Pharmaceuticals San Diego, CA | MAb | treatment of relapsed or refractory low-grade or follicular CD20-positive B-cell non-Hodgkin's lymphoma (November 1997); |

TABLE A-continued

| | | | |
|---|---|---|---|
| Roferon ®-A interferon alfa-2a, recombinant | Hoffmann-La Roche Nutley, NJ | interferon | hairy cell leukemia (June 1986); AIDS-related Kaposi's sarcoma (NPvember 1988); chronic myelogenous leukemia (November 1995); hepatitis C (November 1996) |
| Saizen ® somatropin (rDNA origin) for injection | Serona Laboratories Norwell, MA | human growth hormone | pediatric growth hormone deficiency (October 1996) |
| Serostim ™ somatropin (rDNA origin) for injection | Serono Laboratories Norwell, MA | human growth hormone | treatment of AIDS-associated catabolism/wasting (August 1996); pediatric HIV failure to thrive (February 1998) |
| Verluma ® nofetumomab | Boehringer ingelheim Ridgefield, CT NeoRx Seattle, WA | MAb | detection of small-cell lung cancer (August 1996) |
| Vistide ® cidofovir injection | Gilead Scienced Foster City, CA | nucleotide analogue | cytomegalovirus retinitis in AIDS patients (June 1996) |
| Zenapax ® daclizumab | Hoffman-La Roche Nutley, NJ | MAb | prevention of acute kidney transplant rejection (December 1997) |

The content of this survey has been obtained through government and industry sources based on the latest information.
The information may not be comprehensive. For more specific information about a particular product, contact the individual company directly.
PhRMA internet adress: http://www.pharma.org
Provided as a Public Service by PhRMA. Founded in 1958 as the Pharmaceutical Manufacturers Association.
Copyright © 1998 by the Pharmaceutical Research and Manufacturers of America. Permission to reprint is awarded is proper credit is given.

Pharmaceutical Research and Manufacturers of America
1100 Fifteenth Street, NW
Washington, D.C. 20005
http://www.phrma.org                                Printed on recycled paper. 4/98

Biotechnology Medicines in Development

| Product Name | Company | Product Category | Indication | Development Status |
|---|---|---|---|---|
| *AIDS/HIV INFECTION AND RELATED CONDITIONS* | | | | |
| AD-439 and AD-519 combination | Tanox Biosystems Houston, TX | MAb | HIV infection, AIDS | Phase II |
| AD-439 MAb, anti-HIV to V3 loop of gp120 protein; neutralizing antibody | Tanox Biosystems Houston, TX | MAb | HIV infection, AIDS | Phase II |
| AD-519 MAb, anti-HIV to C4 region of gp120 protein; neutralizing antibody | Tanox Biosystems Houston, TX | MAb | HIV infection, AIDS | Phase II |
| Alferon LDO ® interferon alfa-n3 | Interferon Sciences New Brunswick, NJ | interferon | AIDS-related complex, AIDS | Phase I/II |
| Alferon N injection ® interferon alfa-n3 | Interferon Sciences New Brunswick, NJ | interferon | HIV infection (see also infectious diseases) co-infection (HIV/HCV) | Phase III Phase II |
| ALVAC-MN 12-TMG (vCP205) | Pasteur Merieux Connaught Lyons, France Virogenetics Albany, NY | vaccine | HIV infection | Phase II |
| Ampligen ® | Hemispherx Biopharma New York, NY | interferon | HIV infection (see also cancer, infectious diseases, other) | Phase II |
| autologous gene-modified hematopoietic stem cells | SyStemix Palo Alto, CA | gene therapy | HIV infection | Phase I |
| gene therapy | Cell Genesys Foster City, CA Hoechst Marion Roussel Kansas City, MO | gene therapy | HIV infection | Phase II |
| gp120 vaccine | VaxGen S. San Francisco, CA | vaccine | AIDS | Phase II |

TABLE A-continued

| | | | | |
|---|---|---|---|---|
| HIV-IT(V) Retrovector ™ HIV-1 IIIB enc/rev retroviral vector | Chrion Viagene San Diego, CA | gene therapy | asymptomatic HIV-1 infection | Phase II |
| HIV vaccine (gp120) | Chiron Emeryville, CA | vaccine | AIDS | Phase II |
| interleukin-10 (IL-10) | Schering-Plough Madison, NJ | interleukin | HIV disease (see also autoimmune, digestive, heart, neurologic, respiratory, skin) | Phase I |
| ISIS 2922 fornivirsen | Isis Pharmaceuticals Carlsbad, CA | antisense | cytomegalovirus retinitis | Phase III |
| ISIS 13312 | Isis Pharmaceuticals Carlsbad, CA | antisense | cytomegalovirus retinitis | Phase I |
| Leukine ™ sargramostim (GM-CSF) | Immunex Seattle, WA | colony stimulating factor | adjuvant to AIDS therapy, HIV infection, prevention of infection in HIV patients (see also cancer) | Phase II |
| memantine | Neurobiological Technologies Richmond, CA | | AIDS dementia complex and AIDS-related neuropathic pain (see also diabetes) | Phase II |
| MPL ® immunomodulator vaccine | Ribi ImmunoChem Hamilton, MT | vaccine | AIDS (see also infectious diseases) | Phase I |
| NEUPOGEN ® Filgrastim (rG-CSF) | Amgen Thousand Oaks, CA | colony stimulating factor | treatment and prevention of neutropenia in HIV patients (see also cancer, respiratory) | application submitted |
| Ovidrel ® recombinant human chorionic gonadotropin (r-hCG) | Ares-Serono and Serono Laboratories Norwell, MA | recombinant gonadotropin | Kaposi's sarcoma, AIDS-related hypogonadism (see also infertility) | Phase I/II |
| PEG interleukin-2 | Chiron Emeryville, CA | interleukin | HIV infection in combination with Retrovir ® | Phase II |
| PMPA | Gilead Sciences Foster City, CA | nucleotide analogue | HIV infection, AIDS | Phase II |
| Preveon ™ adefovir dipivoxil | Gilead Sciences Foster City, CA | nucleotide analogue | HIV infection, AIDS | Phase III |
| PRO 367 | Progenics Pharmaceuticals Tarrytown, NY | | HIV infection | Phase I |
| PRO 542 | Progenics Pharmaceuticals Tarrytown, NY | | HIV infection | Phase I |
| Proleukin ® aldesleukin (interleukin-2) | Chiron Emeryville, CA | interleukin | HIV infection in combination with Retrovir ® (see also cancer) | Phase II/III |
| Remune HIV-1 immunogen | Immune Response Corp. Carlsbad, CA | immune-based therapy | HIV seropositive | Phase III |
| retroviral vector with 2 ribozymes | Chiron Emeryville, CA | gene therapy | HIV infection | Phase I/II |
| TBC-38 (vaccinia virus expressing HIV genes env, gag and pal) | Therion Biologics Cambridge, MA | vaccine | AIDS prevention | Phase I |
| AUTOIMMUNE DISORDERS | | | | |
| adensoine deaminase-transduced autologous CD34+ PBC or umbilical cord/ placental blood cells | National Cancer Institute Bethesda, MD | gene therapy | severe combined immunodeficiency | Phase I NCI TRIAL |
| adenosine deaminase-transduced T cells | National Cancer Institute Bethesda, MD | gene therapy | severe combined immunodeficiency | Phase I NCI TRIAL |
| AnergiX ™-RA | Anergen Redwood City, CA | functional antigenics immunotherapy | rheumatoid arthritis | Phase I |
| AnervaX ™ | Anergen Redwood City, CA | peptide vaccine | rheumatoid arthritis | Phase II |

TABLE A-continued

| Name | Company | Type | Indication | Phase |
|---|---|---|---|---|
| Avakine ™ chimeric anti-TNF antibody | Centocor Malvern, PA | MAb | rheumatoid arthritis (see also digestive) | Phase III |
| CD40 ligand antibody | Biogen Cambridge, MA | MAb | lupus, immune thromobocytopenic purpura | Phase II |
| clenoliximab | IDEC Pharmaceuticals San Diego, CA SmithKline Beecham Philadelphia, PA | MAb | rheumatoid arthritis | Phase II |
| ConXn ™ relaxin | Connetics Palo Alto, CA | recombinant human protein | scleroderma | Phase II |
| Enbrel tumor necrosis factor (TNF) receptor | Immunex Seattle, WA Wyeth-Ayerst Laboratories Philadelphia, PA | recombinant soluble receptor | rheumatoid arthritis | Phase III |
| h5G1.1 | Alexion Pharmaceuticals New Haven, CT | MAb | lupus, rheumatoid arthritis | Phase I/II |
| IDEC-131 humanized MAb | IDEC Pharmaceuticals San Diego, CA | MAb | systemic lupus erythermatosus | Phase I |
| IL-2 fusion protein $DAB_{185}IL-2$ | Seragen Hopkinton, MA | fusion protein | severe rheumatoid arthritis (see also cancer, skin) | Phase I/II |
| interleukin-10 (IL-10) | Schering-Plough Madison, NJ | interleukin | rheumatoid arthritis (see also AIDS/HIV, digestive, heart, neurologic, respiratory, skin) | Phase II |
| IR 501 therapeutic vaccine | Immune Response Corp. Carlsbad, CA | vaccine | rheumatoid arthritis | Phase II |
| ISIS 2302 | Isis Pharmaceuticals Carlsbad, CA | antisense | rheumatoid arthritis (see also digestive, skin, transplantation) | Phase II |
| MDX-33 | Medarex Annandale, NJ | MAb | autoimmune diseases, idiopathic thrombocytopenic purpura | Phase I |
| ORTHOCLONE OKT4A | Ortho Biotech Raritan, NJ | MAb | treatment of CD4-mediated autoimmune diseases (see also transplantation) | Phase II |
| Quadrakine interleukin-4 (IL-4) | Schering-Plough Madison, NJ | interleukin | rheumatoid arthritis | Phase I |
| SMART ™ Anti-CD3 HuM291 | Protein Design Labs Mountain View, CA | MAb | autoimmune diseases (see also transplantation) | Phase I |
| BLOOD DISORDERS | | | | |
| CPC-111 | Cypros Pharmaceuticals Carlsbad, CA | cellular therapy | sickle cell disease (see also heart) | Phase II |
| Factor VIII | Transkaryotic Therapies Cambridge, MA | gene therapy | hemophilia A | Phase I |
| GA-EPO | Hoechst Marion Roussel Kansas City, MO Transkaryotic Therapies Cambridge, MA | erythropoietin | anemia associated with chronic renal failure | Phase II |
| Kogenate-N tFVIII | Bayer Berkeley, CA | clotting factor | hemophilia A | Phase III |
| NovoSeven ® recombinant factor Vita | Novo Nordisk Pharmaceuticals Princeton, NJ | clotting factor | treatment of hemophilia A & B with and without antibodies against factors VIII/IX | Phase III |
| Optro ™ recombinant human hemoglobin (rHb1.1) | Somatogen Boudler, CO | recombinant human hemoglobin | oxygen-carrying agent and alternative to red blood caell transfusion | Phase II |
| | | | stimulation of red blood cell formation | Phase I |
| ReFacto ® recombinant factor VIII | Genetics Institute Cambridge, MA | clotting factor | hemophilia A | Phase III |
| YM-337 MAb | Yamanouchi USA White Plains, NY Protein Design Labs Mountain View, CA | MAb | platelet aggregation | Phase I |
| CANCER AND RELATED CONDITIONS | | | | |
| 1311-ChTNT-1/8 | Techniclone Tustin, CA | MAb | malignant glioma | Phase I |
| Aastrom ™ Cell Production System | Aastrom Biosciences Ann Arbor, MI | cellular therapy | cancer immunosuppression/ blood and immune system recovery for patients receiving | Phase II |

TABLE A-continued

| | | | ablative chemotherapy | |
|---|---|---|---|---|
| stem and progenitor cell expansion from bone marrow and umbilical cord blood | | | | |
| Actimmune ® interferon gamma-1b | National Cancer Institute Bethesda, MD Genentech S. San Francisco, CA | interferon | colon, lung, ovarian, prostate cancers, melanoma | Phase II NCI TRIAL |
| AFP-Scan ™ technetium-99m-FAb' fragment (germ cell) | Immunomedics Morris Plains, NJ | MAb | extent of disease staging of liver and germ cell cancers | Phase II |
| allogeneic hematopoietic stem cell transplantation | SyStemix Palo Alto, CA | cellular therapy | advanced leukemia, lymphona, myelodysplastic syndromes | Phase I |
| Allovectin-7 DNA/lipid complex encoding HLA-87 antigen | Vical San Diego, CA | gene therapy | advanced metastatic melanoma, non-resectable squamous cell carcinoma of the head and neck | Phase II |
| ALT (autolymphocyte therapy) | Cellcor Newton, MA CYTOGEN Princeton, NJ | cellular therapy | metastatic renal cell carcinoma (kidney cancer) | Phase III completed |
| ALVAC-87.1 | National Cancer Institute Bethesda, MD | gene therapy | melanoma | Pahse I NCI TRIAL |
| ALVAC-CEA-87.1 | National Cancer Institute Bethesda, MD | gene therapy | advanced adenocarcinomas | Phase I NCI TRIAL |
| ALVAC-CEA vaccine | National Cancer Institute Bethesda, MD | vaccine | advanced cancers | Phase I NCI TRIAL |
| ALVAC-IL-12 vaccine | National Cancer Institute Bethesda, MD Pasteur Merieux Connaught Lyons, France | vaccine | melanoma | Phase I NCI TRIAL |
| Ampligen ® | Hemispherx Biopharma New York, NY | interferon | renal cancer (see also AIDS/HIV, infectious diseases, other) | Phase I/II |
| anti-cancer T-cell gene therapy | Cell Genesys Foster City, CA | gene therapy | colon cancer | Phase I/II |
| anti-idiotype monoclonal antibody | Novartis Pharmaceuticals East Hanover, NJ | MAb | cancer | Phase I |
| anti-Tac(Fv)-PE38 immunotoxin | National Cancer Institute Bethesda, MD | MAb + toxin | leukemia, lymphoma | Phase I NCI TRIAL |
| anti-transferrin receptor MAb | National Cancer Institute Bethesda, MD | MAb | advanced, refractory solid tumors | Phase I NCI TRIAL |
| anti-VEGF humanized MAb | Genentech S. San Francisco, CA | MAb | cancer | Phase I |
| autologous hematopoietic stem cells for autologous hematopoietic transplantation | SyStemix Palo Alto, CA | cellular therapy | hematopoietic reconstitution in patients with multiple myeloma, non-Hodgkin's lymphoma, breast cancer | Phase I/II |
| autologous peptide-specific activated lymphocytes | National Cancer Institute Bethesda, MD | cellular therapy | advanced solid tumors | Phase I NCI TRIAL |
| autologous transduced CD34+ bone marrow and peripheral blood stem cells | National Cancer Institute Bethesda, MD | gene therapy | breast cancer, myeloma | Phase I NCI TRIAL |
| Avicidin ® MAb conjugate | Janssen Pharmaceutics Titusville, NJ NeoRix Seattle, WA | MAb | colorectal, lung, prostate cancers | Phase II |
| Avicine ™ CTP-37 | AVI BioPharma Portland, OR | vaccine | colorectal, pancreatic cancers | Phase II |
| Avonex ® interferon beta-1A | Biogen Cambridge, MA | interferon | glioma (see also neurologic) | Phase II |
| B7 transfected allogeneic melanoma cell vaccine | National Cancer Institute Bethesda, MD | vaccine | melanoma | Phase I NCI TRIAL |
| BEC2, anti-idiotype MAb | ImClone Systems Somerville, NJ | vaccine | melanoma, small-cell lung cancer | Phase I |
| Betaseron ® | National Cancer Institute | interferon | non-small-cell lung cancer | Phase III |

TABLE A-continued

| Name | Company/Location | Type | Indication | Phase |
|---|---|---|---|---|
| recombinant beta interferon-1b | Bethesda, MD Berlex Laboratories Wayne, NJ | | (see also neurologic) | NCI TRIAL |
| bispecific antibody | Chiron Emeryville, CA | MAb | cancer | Phase I |
| C225, anti-EGFR chimeric MAb | ImClone Systems Somerville, NJ | MAb | epidermal growth factor receptor positive cancers | Phase II |
| Campath 1H | LeukoSite Cambridge, MA | Mab | chronic lymphocytic leukemia | in clinical trials |
| carcinoembryonic antigen peptide-1 vaccine | National Cancer Institute Bethesda, MD | vaccine | breast, gastrointestinal tract, lung cancers | Phase I NCI TRIAL |
| CEACide ™ humanized anti-CEA antibody (hMN14) | Immunomedics Morris Plains, NJ | MAb | colorectal cancer | Phase II |
| CEA-Scan ™ technetium-99m-arcitumomab (breast) | Immunomedics Morris Plains, NJ | Mab | extent of disease staging of breast cancer | Phase II |
| CEA-Scan ™ technetium-99m-arcitumomab (lung) | Immunomedics Morris Plains, NJ | MAb | extent of disease staging of lung cancer | Phase III |
| CEAVac ™ anti-idiotype antibody vaccine | Titan Pharmaceuticals S. San Francisco, CA | vaccine | colorectal cancer | Phase II |
| cell therapy | CytoTherapeutics Providence, RI | cellular therapy | cancer pain, untreatable/unrelieved by other forms of treatment | Phase II |
| Cereport ™ (RMP-7) and carboplatin | Alkermes Cambridge, MA | | recurrent malignant brain tumor | Phase III |
| chemotherapy-resistant bone marrow | Genetix Rye, NY | gene therapy | treatment of cancer patients requiring chemotherapy | Phase I/II |
| chimeric MAb 14, 18 | National Cancer Institute Bethesda, MD | Mab | melanoma, neuroblastoma | Phase II NCI TRIAL |
| CM 101 | CarboMed Brentwood, TN | | cancer | Phase I/II |
| CMA-676 | Wyeth-Ayerst Laboratories Philadelphia, PA | Mab | relapsed acute myelogenous leukemia | Phase II/III |
| CMB-401 | Wyeth-Ayerst Laboratories Philadelphia, PA | MAb | ovarian cancer | Phase I/II |
| colon cancer cell line vaccine | Immune Response Corp. Carlsbad, CA Sidney Kimmel Cancer Center San Diego, CA | vaccine | colon cancer | Phase I/II |
| CP-358, 774 | OSI Pharmaceuticals Uniondale, NY Pfizer New York, NY | cellular therapy | cancer | Phase I |
| CT-2584 | Cell Therapeutics Seattle, WA | | ovarian, prostate cancer, sarcoma | Phase I |
| cytosine deaminase gene-adenoviral vector | GenVec Rockville, MD | gene therapy | colon cancer | Phase I |
| DA/Hu(gamma).4 [hiFN-y(V)] Retrivector ™ hiFN-y retroviral vector | Chiron Viagene San Diego, CA | gene therapy | metastatic melanoma | Phase I |
| DA/Hu(gamma), 15-transduced autologous tumor cells and interferon-gamma expressing transduced autologous tumor cells (combination therapy) | Chiron Viagene San Diego, CA | gene therapy | stage IV malignant melanoma | Phase I |
| DA/Hu(gamma), 15-transduced autologous tumor cells; ITAT | Chiron Viagene San Diego, CA | gene therapy | disseminated malignant melanoma | Phase I |
| dariplestim | Searle Skokie, IL | growth factor | mobilization of peripheral blood stem cells | Phase III |
| dendritic cell therapy | Dendreon Mountain View, CA | cellular therapy | advanced prostate cancer multiple myeloma | Phase II/III Phase I |
| E/A lipid complex | Targeted Genetics | gene therapy | breast, head and neck, ovarian | Phase I |

TABLE A-continued

| Name | Company/Location | Type | Indication | Phase |
|---|---|---|---|---|
| (rgDCC-E/A) | Seattle, WA | | cancers | |
| EGF fusion protein DAB$_{389}$EGF | Seragen Hopkinton, MA | fusion protein | non-small-cell lung cancer | Phase I/II |
| EPREX ® erythropoietin | National Cancer Institute Bethesda, MD Ortho Biotech Raritan, NJ | erythropoietin | neuroblastoma | Phase II NCI TRIAL |
| ERB-38 immunotoxin fusion protein (recombinant) | National Cancer Institute Bethesda, MD | fusion protein | advanced stage solid tumors | Phase I NCI TRIAL |
| Ewing's sarcoma and alveolar rhabdomyosarcoma peptide vaccine | Natioanl Cancer Institute Bethesda, MD | vaccine | sarcoma | Phase I NCI TRIALS |
| FLT3 ligand | National Cancer Institute Bethesda, MD Immunex Seattle, WA | growth factor | melanoma, renal cell cancer | Phase I NCI TRIAL |
| G3139 | Genta San Diego, CA | antisense | cancer | Phase I |
| gamma interferon gene therapy | Chiron Emeryville, CA | gene therapy | cancer | Phase I |
| Gastrimmune ™ neutralizing G17 hormone | Aphton Woodland, CA | vaccine | colorectal, pancreatic, stomach cancers (see also digestive) | Phase I/II |
| GeneVax ® gene vaccine | Centocor Malvern, PA | vaccine | colorectal cancer | Phase I |
| GLI-328 | Genetic Therapy Gaithersburg, MD | gene therapy | glioblastoma multiforme | Phase III |
| GM-CSF cellular cancer vaccine | Powderject Vaccines Madison, WI | vaccine | melanoma, sarcoma | Phase I |
| GMK ganglioside antigen | Bristol-Myers Squibb Princeton, NJ Progencis Pharmaceuticals Tarrytown, NY | vaccine | prevent recurrence following surgery to remove primary melanoma | Phase III |
| gp100 adenovirus vaccine | National Cancer Institute Bethesda, MD Genzyme Molecular Oncology Cambridge, MA | vaccine | melanoma | Phase I NCI TRIAL |
| gp100 peptide vaccine | National Cancer Institute Bethesda, MD | vaccine | melanoma | Phase I NCI TRIAL |
| GVAX ™ cancer vaccine | Cell Genesys Foster City, CA | vaccine | prostate, lung cancers, melanoma | Phase I/II |
| HER-2/neu peptide vaccine | National Cancer Institute Bethesda, MD | vaccine | breast, colorectal, ovarian, prostate cancers | Phase I NCI TRIAL |
| Herceptin ™ trastuzumab (anti-HER-2 humanized MAb) | Genentech S. San Francisco, CA | MAb | breast cancer | Phase III completed |
| HPV 16, E6 and E7 peptide vaccine | National Cancer Institute Bethesda, MD | vaccine | cervical cancer | Phase I NCI TRIAL |
| HPV E7 lipopeptide vaccine | National Cancer Institute Bethesda, MD Cytel San Diego, CA | vaccine | cervical cancer | Phase I NCI TRIAL |
| HPV vaccine | Medimmune Gaithersburg, MD SmithKline Beecham Philadelphia, PA | vaccine | cervical cancer (see also infectious disease) | Phase I |
| HSPPC-96 (autologous tumor derived) | Antigenics New York, NY | heat shock portein | melanoma, pancreatic, renal cell cancers | Phase I |
| human growth hormone | Transkaryotic Therapies Cambridge, MA | gene therapy | cancer cachexia (muscle wasting) | Phase I |
| IDEC-In88 | IDEC Pharmaceuticals San Diego, CA | Mab | non-Hodgkin's B-cell lymphoma | Phase I/II |
| IDEC-Y288 | IDEC Pharmaceuticals San Diego, CA | MAb | non-Hodgkin's B-cell lymphoma | Phase I/II |
| Leucotropin GM-CSF | Cangene Mississauga, Ontario | colony stimulating factor | mobilization of peripheral blood stem cells in patients with adjuvant breast cancer | Phase III |
| Leukine ™ sargramostin (GM-CSF) | Immunex Seattle, WA | colony stimulating factor | prophylaxis and treatment of chemotherapy-induced neutropenia, prophylaxis of chemotherapy-induced neutropenia in acute myelogenous leukemia (see also AIDS/HIV) | application submitted |

TABLE A-continued

| | | | | |
|---|---|---|---|---|
| Lervectin DNA/lipd complex encoding IL-2 | Vical San Diego, CA | gene therapy | prostate cancer, renal cell carcinoma, melanoma, sarcoma | Phase I |
| LP 2307 | LIDAX Pharmaceuticals La Jolla, CA | vaccine | malignant melanoma | Phase I/II |
| LR-3001 | Inex Pharmaceuticals Hayward, CA | antisense | chronic myelogenous leukemia in accelerated phase or blast crisis | Phase I |
| LYM-T | Techniclone Tustin, CA | MAb | lymphoma | Phase II/III |
| Lymphocide ™ anti-CD22 humanized MAb | Immunomedics Morris Plains, NJ | MAb | non-Hodgkin's B-cell lymphoma | Phase I/II |
| LymphoScan ™ technetium-99m-bectumomab (lymphoma) | Immunomedics Morris Plains, NJ | MAb | extent of disease staging of non-Hodgkin's B-cell lymphoma, detection of residual disease following radiation/chemotherapy | Phase III |
| Mab | Glaxo Wellcome Rsch, Triangle Park, NC | Mab | lung, prostate cancers | Phase II |
| MART-1 adenvirus vaccine | National Cancer Institute Bethesda, MD Genzyme Molecular Oncology Cambridge, MA | vaccine | melanoma | Phase I NCI TRIAL |
| MART-1 melanoma vaccine | National Cancer Institute Bethesda, MD | vaccine | metastatic melanoma | Phase I NCI TRAIL |
| MDRx1 ™ | Titan Pharmaceuticals S. San Francisco, CA | gene therapy | enable high-dose chemotherapy with reduced side effects | Phase I |
| MDX-447 bispecific antibody | Medarex Annandale, NJ | Mab | head and neck, renal cancers | Phase I/II |
| MDX-H210 bispecific antibody | Medarex Annandale, NJ | MAb | breast, colorectal, kidney, ovarian, prostate cancers | Phase I/II |
| Melacine ® melanoma | Ribi ImmunoChem Hamilton, MT | vaccine | stage IV melanoma with interferon alpha | Phase III completed |
| theraccine (therapeutic vaccine | Ribi ImmunoChem Hamilton, MT Southwest Oncology Group San Antonio, TX | vaccine | stage II melanoma in patients with no evidence of disease to prevent recurrence following surgery to remove primary disease | Phase III |
| myeloid progenitor inhibitory factor-1 | Human Genome Sciences Rockville, MD | interleukin | chemoprotection | Phase I |
| myeloma-derived idiotypic antigen vaccine | National Cancer Institute Bethesda, MD | vaccine | multiple myeloma | Phase I NCI TRIAL |
| NEUPOGEN ® Filgrastim (rG-GSF) | Amgen Thousand Oaks, CA | colony stimulating factor | acute myelogenous leukemia (see also AIDS/HIV, respiratory) | application submitted |
| Oncaspar ® PEG-L-asparaginase | Enzon Piscataway, NJ Rhone-Poulenc Rorer Titusville, NJ | | first-line treatment of acute lymphoblastic leukemia (ALL) adult ALL non-Hodgkin's lymphoma, chronic lymphocytic leukemia | in clinical trials |
| Oncolym ® | Techniclone Tustin, CA | MAb | malignant glioma | Phase I |
| Oncoltad ® PR CYT-356-Y-90 | CYTOGEN Princeton, NJ | MAb | targeted radiotherapy for prostate malignancies | Phase II |
| OncoScint ® CR/OV satumomab pendetide | CYTOGEN Princeton, NJ | MAb | detection, staging and follow-up of breast cancer | Phase II |
| ONYX-015 | Onyx Pharmaceuticals Richmond, CA | oncolytic virus therapy | p53 deficient cancers | Phase I/II |
| p53 and RAS vaccine | National Cancer Institute Bethesda, MD | vaccine | solid tumors | Phase I NCI TRIAL |
| p53 tumor suppressor gene | Schering-Plough Madison, NJ | gene therapy | lung cancer solid tumors that carry the p53 gene mutation or deletion | Phase II Phase I |
| Panorex ® edrecolomab | Centocor Malvern, PA | MAb | adjuvant therapy for post-operative colorectal cancer | Phase III |
| peripheral blood lymphocytes transduced with a gene encoding a chimeric T-cell receptor | National Cancer Institute Bethesda, MD | gene therapy | ovarian cancer | Phase I NCI TRIAL |
| Proleukin ® aldesleukin (interleukin-2) | Chiron Emeryville, CA | interleukin | acute myelogenous leukemia, (see also AIDS/HIV) | Phase II/III non-Hodgkin's lymphoma |
| promegapoetin | Searle Skokie, IL | growth factor | adjunctive hematopoietic therapy following chemotherapy | Phase I |

TABLE A-continued

| | | | | |
|---|---|---|---|---|
| Prostrac recombinant vaccinia virus | Therion Biologics Cambridge, MA | vaccine | prostate cancer | Phase I/II |
| RA5 5-17 peptide vaccine | National Cancer Institute Bethesda, MD | vaccine | solid tumors | Phase I NCI TRIAL |
| rCEA Vaccine recombinant carcinoembryonic antigen | Protein Sciences Meriden, CT | vaccine | breast, colon cancers | Phase I |
| Rebi ® recombinant interferon beta-1a | Serono Laboratories Norwell, MA | interferon | colorectal cancer (see also infectious diseases, neurologic) | Phase III |
| recombinant human interleukin-12 (rhIL-12) | Genetics Institute Cambridge, MA Wyeth-Ayerst Laboratories Philadelphia, PA | interleukin | non-small-cell lung cancer cancer (see also infectious diseases) | Phase I/II Phase I/II |
| retroviral vector with tumor necrosis factor gene | Chiron Emeryville, CA | gene therapy | melanoma | Phase I |
| rf-gp100 (recombinant fowlpox virus) | Therion Biologics Cambridge, MA | vaccine | melanoma | Phase I |
| rF-MART-1 (recombinant fowlpox virus) | Therion Biologics Cambridge, MA | vaccine | melanoma | Phase I |
| RIGScan ® CR49 125 I-cc49 MAb | Neoprobe Dublin, OH | MAb | colorectal cancer | application submitted |
| Rituxan ® rituximab | National Cancer Institute Bethesda, MD IDEC Pharmaceuticals San Diego, CA | Mab | leukemia, lymphoma | Phase II NCI TRIAL |
| Roferon ®-A interferon alfa-2a, recombinant | Hoffmann-La Roche Nutley, NJ | interferon | malignant melanoma adjuvant | Phase III |
| rV-gp100 (recombinant vaccinia virus) | Therion Biologics Cambridge, MA | vaccine | melanoma | Phase I |
| rV-MART-1 (recombinant vaccinia virus) | Therion Biologics Cambridge, MA | vaccine | melanoma | Phase I |
| Serostim ™ somatropin (rDNA origin) for injection | Serono Laboratories Norwell, MA | human growth hormone | cancer cachexia (see also other) | Phase I/II |
| Sigoslx ® recombinant interleukin-6 (r-IL-6) | Ares-Serono and Serono Laboratories Norwell, MA | interleukin | hematological conditions (myelodysplastic syndromes, cancer) | Phase I/II |
| SMART ™ M195 HuM195 | Protein Design Labs Mountain View, CA | MAb | acute myeloid leukemia acute promyelocytic leukemia advanced myeloid leukemia (with Bismuth-213) | Phase II/III Phase II Phase I |
| stem cell factor | Amgen Thousand Oaks, CA | stem cell factor | adjunct to chemotherapy | application submitted |
| SU101 | SUGEN Redwood City, CA | PDGF-receptor tyrosine kinase inhibitor | malignant glioma prostate cancer solid tumors | Phase III Phase II Phase I/II |
| SUS416 | SUGEN Redwood City, CA | angiogenesis inhibitor | solid tumors | Phase I |
| TBC CEA (vaccinia virus expressing carcinoembryonic antigen) | Therion Biologics Cambridge, MA | vaccine | colorectal and lung cancers | Phase I/II |
| TCell-HDM | Coulter Cellular Therapies Boston, MA | cellular therapy | cancer | Phase I/II |
| Theratope ® synthetic carbohydrate therapeutic vaccine | Biomira Edmonton, Alberta Chiron Emeryville, CA | vaccine | breast cancer | Phase II completed |
| thrombopoietin | Genentech S. San Francisco, CA | erythropoietin | thrombocytopenia related to cancer treatment | Phase II |

TABLE A-continued

| Name | Company | Type | Indication | Status |
|---|---|---|---|---|
| Thyrogen ® recombinant human thyroid-stimulating hormone | Genzyme Cambridge, MA | | detection and treatment of thyroid cancer metastases | application submitted |
| TNT | Techniclone Tustin, CA | MAb | non-Hodgkin's B-cell lymphoma solid tumors | Phase II/III Phase I |
| TriAB ™ anti-idiotype antibody vaccine | Titan Pharmaceuticals S. San Francisco, CA | vaccine | breast cancer | Phase II |
| TriGEM ™ anti-idiotype antibody vaccine | Titan Pharmaceuticals S. San Francisco, CA | vaccine | small-cell lung cancer, melanoma | Phase I |
| urate oxidase (recombinantly-produced enzyme) | Sanoli New York, NY | recombinant enzyme | prophylaxis for chemotherapy-related hyperuricemia, treatment of cancer-related hyperuricemia | Phase III |
| vaccine-CEA 180KD vaccine | National Cancer Institute Bethesda, MD Therion Biologics Cambridge, MA | vaccine | advanced colorectal cancer | Phase I NCI TRIAL |
| Vaxid anti-idiotype DNA vaccine | Vical San Diego, CA | vaccine | B-cell and mantle cell lymphomas | Phase I |
| Xerecept ™ human corticorropin-releasing factor (hCRF) | Neurobiological Technologies Richmond, CA | | brain tumor edema | Phase II |
| Zenapax ® daclizumab | Hoffmann-La Roche Nutley, NJ Protein Design Labs Mountain View, CA | Mab | certain blood cancers (see also eye, neurologic, skin, transplantation) | Phase II |
| DIABETES AND RELATED CONDITIONS | | | | |
| Beta Kline transforming growth factor-beta 2 | Genzyme Tissue Repair Cambridge, MA | growth factor | chronic diabetic foot ulcers | Phase II |
| BetaRx-H encapsulated human islets | VivoRx Santa Monica, CA | cellular therapy | insulin-dependent diabetes | Phase I |
| BetaRx-P encapsulated procine islets | VivoRx Santa Monica, CA | cellular therapy | insulin-dependent diabetes | Phase I |
| BetaRx-Pr encapsulated proliferated human islets | VivoRx Santa Monica, CA | cellular therapy | insulin-dependent diabetes | Phase I |
| Glucagen ™ recombinant human glucagen (protein) | Novo Nordisk Pharmaceuticals Princeton, NJ | recombinant human protein | hypoglycemia (see also digestive) | Phase III |
| glucagen for injection (rDNA origin) | Eli Lilly Indianapolis, IN | recombinant human protein | to treat severe hypoglycemic events in patients with diabetes and to aid in gastrointestinal diagnostic procedures | application submitted |
| insulinotropin | Scios Mountain View, CA | | type 2 diabetes | Phase II |
| memantine | Neurobiological Technologies Richmond, CA | | painful diabetic neuropathy (see also AIDS/HIV) | Phase II |
| nerve growth factor | Genentech S. San Francisco, CA | growth factor | diabetic peripheral neuropathy | Phase III |
| pirnagedine | Alteon Ramsey, NJ Genentech S. San Francisco, CA | | diabetic progressive kidney disease, diabetic end-stage kidney disease (see also neurologic) | Phase III |
| pramlintide | Amylin Pharmaceuticals San Diego, CA | human amylin analog | improved metabolic control, which includes glucose, weight and lipid profiles in type 1 and insulin-using type 2 diabetes | Phase III |
| rDNA insulin | Inhale Therapeutic Systems Palo Alto, CA | recombinant insulin | diabetes | Phase II |
| Trovert ™ | Sensus Austin, TX | human growth hormone | diabetes-related illnesses (see also growth disorders) | Phase II |
| DIGESTIVE DISORDERS | | | | |
| Avakine ™ chimeric anti-TNF antibody | Centocor Malvern, PA | Mab | Crohn's disease (see also autoimmune) | application submitted |

TABLE A-continued

| | | | | |
|---|---|---|---|---|
| Gastrimmune ™ neutralizing G17 hormone | Aphton Woodland, CA | vaccine | gastroesphageal reflux disease, peptic and nonsteroidal anti-inflammatory drug ulcers (see also cancer) | Phase I/II |
| Glucagen ™ recombinant human glucagen (protein) | Novo Nordisk Pharmaceuticals Princeton, NJ | recombinant human protein | gastrointestinal motility inhibition (see also diabetes) | Phase III |
| interleukin-10 (IL-10) | Schering-Plough Madison, NJ | interleukin | Crohn's disease, ulcerative colitis (see also AIDS/HIV, autoimmune, heart, neurologic, respiratory, skin) | Phase II |
| ISIS 2302 | Isis Pharmaceuticals Carlsbad, CA | antisense | Crohn's disease, ulcerative colitis (see also autoimmune, skin, transplanatation) | Phase II |
| LDP-02 | Genentech S. San Francisco, CA LeukoSite Cambridge, MA | MAb | inflammatory bowel disease | Phase II |
| LeukoScan ® sulesomab | Immunomedics Morris Plains, NJ | MAb | inflammatory bowel disease (see also infectious diseases) | Phase II |
| Neurnega ® recombinant human interleukin-11 | Genetics Institute Cambridge, MA | interleukin | Crohn's disease | Phase II |
| recombinant platelet activating factor-acetyllhydrolase (rPAF-AM) | ICOS Bothell, WA | | pancreatitis (see also respiratory) | Phase II |
| EYE CONDITIONS | | | | |
| BPD-MA verteporfin | QLT Photo Therapeutics Vancouver, British Columbia | | age-related macular degeneration | Phase III |
| MDX-RA immunotoxin | Medarex Annandale, NJ | Mab | prevention of secondary cataract | Phase III |
| Zenapax ® daclizumab | Hoffmann-La Roche Nutley, NJ Protein Design Labs Mountain View, CA | Mab | uveitis (see also cancer, neurologic, skin, transplantation) | Phase I/II |
| GENETIC DISORDERS | | | | |
| AAV CFTR gene therapy | Targeted Genetics Seattle, WA | gene therapy | cystic fibrosis (see also respiratory) | Phase I |
| CFTR/adenovirus vector | Genzyme Cambridge, MA | gene therapy | cystic fibrosis | Phase I |
| CFTR/lipid vector | Genzyme Cambridge, MA | gene therapy | cystic fibrosis | Phase I |
| ex vivo stem cells/ retrovirus vector | Genzyme Cambridge, MA | gene therapy | Gaucher's disease | Phase I |
| GR2134878 | Glaxo Wellcome Rsch, Triangle Park, NC Megabios Burlingame, CA | gene therapy | cystic fibrosis | Phase I/II |
| GV-10 | GenVec Rockville, MD | gene therapy | cystic fibrosis | Phase I |
| HP-3 | Milkhaus Laboratory Boxford, MA | signalling | cystic fibrosis | Phase II |
| Neuprex ™ recombinant human bactericidal/ permeability-increasing protein (rBPI-21) | XOMA Berkeley, CA | recombinant human protein | cystic fibrosis exacerbations (see also infectious diseases, other) | Phase I |
| Pulmozyme ® domase alpha, recombinant | Genentech S. San Francisco, CA | recombinant DNase | early intervention in cystic fibrosis | Phase III |
| x-galachosidase A | Transkaryotic Therapies Cambridge, MA | enzyme | Fabry' disease | Phase I |
| GROWTH DISORDERS | | | | |
| pralmorelin (GPA-748) | Wyeth-Ayerst Laboratories Philadelphia, PA | human growth hormone | adult growth hormone deficiency | Phase I |
| ProLease ® hGH | Alkermes Cambridge, MA Genentech S. San Francisco, CA | human growth hormone | growth hormone deficiency in children | Phase III |
| Saizen ® somatropin (rDNA origin) | Serono Laboratories Norwell, MA | human growth hormone | management of adults with growth hormone disorder, intrauterine growth retardation in children | Phase III |

TABLE A-continued

| Name | Company | Type | Indication | Phase |
|---|---|---|---|---|
| for injection Trovert ™ | Sensus Austin, TX | human growth hormone | (see also other) acromegaly (see also diabetes) | Phase II |
| | | | HEART DISEASE | |
| AcuTect ™ Tc-99m apcitide | Diatide Londonderry, NH | peptide | detection of carotid thrombus | Phase II |
| anti-CD18 humanized MAb | Genentech S. San Francisco, CA | MAb | acute myocardial infarction | Phase II |
| BioByPant ™ therapeutic angiogenesis (VEGF) | CenVec Rockville, MD | gene thearpy | cardiovascular disease, including cardiac artery disease and peripheral vascular disease, either as an adjunct or alternative to existing surgical approaches such as cardiac artery approaches such as cardiac artery bypass grafts and angioplasty | Phase I |
| Biostent ™ | NeoRx Seattle, WA | | reduction of restinosis (vascular remodeling) following balloon angioplasty | Phase I |
| Capiscint | Centocor Malvern, PA | MAb | atherosclerotic plaque imaging agent | Phase I |
| Corsevin ™ M 12D10-Fab | Centocor Malvern, PA Corvas San Diego, CA | MAb | thrombolytic complications of percutaneous transluminal coronary angioplasty, coronary arterial starts, disseminates intravascular coagulation | Phase I |
| CPC-111 | Cypros Pharmaceuticals Carlsbad, CA | cellular therapy | coronary bypass surgery (see also blood) | Phase II |
| factor VIIa inhibitors | Corvas San Diego, CA | | deep vein thrombosis, pulmonary embolism, unstable angina, myocardial infarction | Phase I |
| FIBLAST ® trafermin | Scios Mountain View, CA Wyeth-Ayerst Laboratories Philadelphia, PA | growth factor | peripheral vascular disease, coronary artery disease (see also neurologic) | Phase II |
| gene therapy | Collateral Therapeutics San Diego, CA | gene therapy | stable exertional angina | Phase I/II |
| growth factor | Chiron Emeryville, CA | growth factor | coronary artery disease | Phase I |
| h5G1.1-SCFV (recombinant) | Alexion Pharmaceuticals New Haven, CT Enzon Piscataway, NJ | | cardiopulmonary bypass-associated inflammation using SCD ® technology | Phase II |
| Hu23F2G MAb | ICOS Bothell, WA | MAb | myocardial infarction (see also neurologic, other) | Phase II |
| integrillin ™ eptifibatide (IIb/IIIa platelet aggregation inhibitor) | COR Therapeutics S. San Francisco, CA Schering-Plough Madison, NJ | | percutaneous transluminal coronary angioplasty, unstable angina acute myocardial infarction | application submitted Phase II |
| interleukin-10 (IL-10) | Schering-Plough Madison, NJ | interleukin | ischemic reperfusion injury (see also AIDS/HIV, autoimmune, digestive, neurologic, respiratory, skin) | Phase I |
| lanoteplase | Bristol-Myers Squibb Princeton, NJ | t-PA | acute myocardial infarction | Phase III |
| LR-3280 | Inex Pharmaceuticals Vancouver, BC Schwarz Pharma Milwaukee, WI | antisense | cardiovascular restinosis | Phase II |
| MH1-Fab' imaging agent | American Biogenetic Sciences Boston, MA | MAb | in vivo imaging agent for the detection of cardiovascular thrombosis | Phase I/II |
| MPL ®-C immunomodulator | Ribi ImmunoChem Hamilton, MT | | prevention/amelioration of cardiac ischemia reperfusion injury | Phase II |
| Natrecor ® BNP | Scios Mountain View, CA | | acute congestive heart failure | Phase III completed/ application submitted |
| Novastan ® argatroban | Texas Biotechnology Houston, TX | | cardiovascular pulmonary surgery heparin-induced thrombocytopenia thrombosis syndrome | Phase I application submitted |
| ReoPro ® abciximab | Centocor Malvern, PA Eli Lilly Indianapolis, IN | MAb | unstable angina (see also neurologic) acute myocardial infarction | Phase III Phase II |
| rhAntithrombin III | Genzyme | | control of blood clotting during | Phase II |

TABLE A-continued

| Name | Company | Type | Indication | Status |
|---|---|---|---|---|
| (recombinant) TNK (secondpgeneration t-PA) | Cambridge, MA Genentech S. San Francisco, CA | t-PA | coronary artery bypass surgery acute myocardial infarction | completed Phase III |
| TP10 | T Cell Sciences Needham, MA | recombinant soluble receptor | heart attack (see also respiratory, transplantation) | Phase I |
| VEGF | Genentech S. San Francisco, CA | growth factor | coronary artery disease | Phase I |
| VEGF 121 (vascular endothelial growth factor) | Scios Mountain View, CA | growth factor | cardiovascular disorders | Phsae I |
| Xubix ™ sibratiban oral IIb/IIIa antagonist | Genentech S. San Francisco, CA | | acute coronary syndrome | Phase III |
| INFECTIOUS DISEASES | | | | |
| adefovir dipivoxil | Gilread Sciences Foster City, CA | nucleotide analogue | hepatitis B | Phase II |
| Alferon N Gel ® interferon alfa-n3 | Interferon Sciences New Brunswick, NJ | interferon | human papillornavirus infections | Phase II |
| Alferon N injection ® interferon alfa-n3 | Interferon Sciences New Brunswick, NJ | interferon | chronic hepatitis C infections (see also AIDS/HIV) genital warts | Phase III Phase II |
| Ampligen ® | Hemispherx Biopharma New York, NY | interferon | hepatitis (see also AIDS/HIV, cancer, other) | Phase I/II |
| anti-tumor necrosis factor MAb | Chiron Emeryville, CA | MAb | sepsis | Phase II/III |
| *Campylobacter* vaccine | Antex Biologics Gaithersburg, MD | cellular vaccine | traveler's diarrhea (*Campylobacter* infections) | Phase II |
| CMV vaccine | Chiron Emeryville, CA | vaccine | cytomegalovirus infection | Phase II |
| DTaP vaccine | Chiron Emeryville, CA | vaccine | diphtheria, tetanus, acellular pertussis | Phase III |
| Epstein-Barr virus vaccine | Aviron Mountain View, CA SmithKline Beecham Philadelphia, PA | recombinant subunit vaccine | prevention of Epstein-Barr virus infection (Cause of mononucleosis infection) | Phase I |
| genital herpes vaccine | Glaxo Wellcome Rsch. Triangle Park, NC | vaccine | genital herpes | Phase I |
| *Helicobacter* vaccine | Antex Biologics Gaithersburg, MD | cellular vaccine | peptic ulcers (*Helicobacter pylori* infections) | Phase I |
| hepatitis A vaccine | Chiron Emeryville, CA | vaccine | hepatitis A | Phase III |
| hepatitis B DNA vaccine | Powderject Vaccines Madison, WI | DNA vaccine | hepatitis B prevention | Phase I |
| hepatitis B vaccine (recombinant) | SmithKline Beecham Philadelphia, PA | vaccine | treatment of hepatitis B | Phase II |
| herpes simplex vaccine (recombinant) | SmithKline Beecham Philadelphia, PA | vaccine | prevention of herpes simplex infection | Phase III |
| HPV vaccine | Medimmune Gaithersburg, MD SmithKline Beecham Philadelphia, PA | vaccine | genital warts (see also cancer) | Phase I |
| human anti-hepatitis B antibody (OST 577) | Protein Design Labs Mountain View, CA | MAb | liver transplantation due to chronic hepatitis B infection | Phase I/II completed |
| Intron ® A interferon alfa-2b (recombinant) | Schering-Plough Madison, NJ | interferon | pediatric hepatitis B, self-injectable closing system for hepatitis C (see also cancer) hepatitis C(PEG-Intron A) | application submitted Phase III |
| intron ® A/ Rebelol ™ interferon alfa-2b (recombinant)/ ribavirin | Schering-Plough Madison, NJ | interferon | relapsed hepatitis C naive hepatitis C(not previously treated with interferon) hepatitis C (PEG-intron A/Rebetol) | application submitted Phase III Phase I |
| LeukoScan ® sulesomab | immunomedics Morris Plains, NJ | MAb | diagnosis of osteomyelitis, infected prosthesis, appendicitis (see also digestive) | application submitted |
| Lyme borreliosis protein vaccine | Pasteur Merieux Connaught Swiftwater, PA | vaccine | Lyme disease | Phase III |
| Lyme disease vaccine (recombinant) | SmithKline Beecham Philadelphia, PA | vaccine | prevention of Lyme disease | application submitted |

TABLE A-continued

| | | | | |
|---|---|---|---|---|
| MAK 195F | Knoll Pharmaceutical Mt. Olive, NJ | Mab | sepsis | Phase III |
| MEDI-491 parvovirus B 19 vaccine | Mediummune Gaithersburg, MD | vaccine | B 19 parvovirus-induced miscarriage and anemia | Phase I |
| meningococcus C vaccine | Chiron Emeryville, CA | vaccine | meningococcus C | Phase II |
| MPL ® immunomodulator (25+ antigens for adult and pediatric applications) | Ribi ImmunoChem Hamilton, MT | vaccine | infectious diseases (see also AIDS/HIV) | in clinical trials |
| Neuprex ™ recombinant human bactericidal/ permeability-increasing protein (rBPI-21) | XOMA Berkeley, CA | recombinant human protein | meningococcemia (see also genetic, other) antibiotic adjuvant in intra-abdominal infections | Phase III Phase II |
| Protovir ™ human anti-CMV antibody | Protein Design Labs Mountain View, CA | MAb | cytomegalovirus infections in bone marrow transplant patients | Phase II completed |
| Rebii ® recombinant interferon beta-1a | Serono Laboratories Norwell, MA | interferon | viral infections (see also cancer, neurologic) | Phase II/III |
| recombinant human activated protein C (rhAPC) | Eli Lilly Indianapolis, IN | recombinant human protein | treatment of seven sepsis | Phase II |
| recombinant human interleukin-12 (rhIL-12) | Genetics Institute Cambridge, MA Wyeth-Ayerst Laboratories Philadelphia, PA | interleukin | infectious diseases (see also cancer) | Phase I/II |
| Rotashield ™ rotavirus vaccine, live, oral, tetravalent | Wyeth-Lederle Vaccine & Pediatrics Philadelphia, PA | continuous cell line vaccine | prevention of rotaviral gastroenteritis in infants | application submitted |
| rotavirus vaccine | Virus Research Institute Cambridge, MA | vaccine | rotavirus in infants | Phase II |
| Savvy ™ C31G | Biosyn Philadelphia, PA | microbicide | infectious disease | Phase I |
| Tenefuss ® Ienercept (TNF-receptor) fusion protein) | Hoffmann-La Roche Nutley, NJ | recombinant soluble receptor | septic shock, severe sepsis | Phase III |
| tifacogin | Chiron Emeryville, CA Searle Skokie, IL | tissue factor pathway inhibitor | sepsis | Phase II |
| | | INFERTILITY | | |
| Anfide ™ gonadotropin hormone-releasing hormone antagonist (GhRHA) | Ares-Serono and Serono Laboratories Norwell, MA | hormone-releasing hormone antagonist | female infertility | Phase I |
| Gonal-P ® recombinant human follicle-stimulating hormone (r-FSH) | Serono Laboratories Norwell, MA | recombinant fertility hormone | male infertility | Phase III |
| LhADI ® recombinant human leutinizing hormome (r-hLH) | Ares-Serono and Serono Laboratories Norwell, MA | recombinant fertility hormone | female infertility-follicular support, stimulation of follicular development | Phase II/III |
| Ovidrel ® recombinant human chorionic gonadotropin (r-hCG) | Ares-Serono and Serono Laboratories Norwell, MA | recombinant gonadotropin | female infertility (see also AIDS/HIV) | Phase III |
| | | NEUROLOGIC DISORDERS | | |
| Activase ™ alteplase, recombinant | Genentech S. San Francisco, CA | t-PA | acute ischemic stroke within 3 to 5 hours of symptom onset | Phase III |
| AnerglX ® MS | Anergen Redwood City, CA | functional antigenics immuno-therapy | multiple sclerosis | Phase I |
| Antigen | Athena Neurosciences | MAb | multiple sclerosis flares | Phase II |

TABLE A-continued

| | | | | |
|---|---|---|---|---|
| natalizumab | S. San Francisco, CA | | | |
| ATM027 humanized MAb | T Cell Sciences Needham, MA | MAb | multiple sclerosis | Phase I |
| Avonex ® interferon beta-1a | Biogen Cambridge, MA | interferon | secondary, progressive multiple sclerosis (see also cancer) | Phase III |
| Betaseron ® recombinant interferon beta-1b | Berlex Laboratories Wayne, NJ Chiron Emeryville, CA | interferon | chronic progressive multiple sclerosis (see also cancer) | Phase III |
| brain-derived neurotrophic factor (BDNF) | Amgen Thousand Oaks, CA Regeneron Pharmaceuticals Tarrytown, NY | growth factor | arryotrophic lateral sclerosis | Phase I |
| CPC-211 | Cypros Pharmaceuticals Carlsbad, CA | cellular therapy | ischermic stroke, traumatic brain injury | Phase II |
| enlimomab (anti-ICAM-1 MAb) | Boehringer Ingelheim Pharmaceuticals Ridgefield, CT | MAb | stroke (see also other) | Phase II/III |
| FIBLAST ® trafermin | Scios Mountain View, CA Wyeth-Ayerst Laboratories Philadelphia, PA | growth factor | stroke (see also heart) | Phase II/III |
| Hu23F2G MAb | ICOS Bothell, WA | MAb | multiple sclerosis, ischemic stroke (See also heart, other) | Phase II |
| interleukin-10 (IL-10) | Schering-Plough Madison, NJ | interleukin | multiple sclerosis (see also AIDS/HIV, autoimmune, digestive, heart, respiratory, skin) | Phase I |
| IR 208 therapeutic vaccine | Immune Response Corp. Carlsbad, CA | vaccine | multiple sclerosis | Phase I |
| LDP-01 | LeukoSite Cambridge, MA | MAb | stroke (see also transplantation) | Phase I/II |
| MS-TCR | Connetics Palo Alto, CA | vaccine | multiple sclerosis | Phase I/II |
| Myotrophin ® rhIGF-1 | Cephalon West Chester, PA Chiron Emeryville, CA | growth factor | amyotrophic lateral sclerosis peripheral neuropathies | application submitted Phase II |
| NeuroCell ™-FE (cellular transplantation therapy) | Diacrin Charlestown, MA | cellular therapy | focal epilepsy | Phase I |
| NeuroCell ™-HD (cellular transplantation therapy) | Diacrin Charlestown, MA Genzyme Tissue Repair Cambridge, MA | cellular therapy | Huntington's disease | Phase I completed |
| NeuroCell ™-PD (cellular transplantation therapy) | Diacrin Charlestown, MA Genzyme Tissue Repair Cambridge, MA | cellular therapy | Parkinson's disease | Phase II |
| neutrophin-3 | Amgen Thousand Oaks, CA Regeneron Pharmaceuticals Tarrytown, NY | growth factor | enteric neuropathics | Phase I/II |
| pimagedine | Alteon Ramsey, NJ Genentech S. San Francisco, CA | | overt neuropathy (see also diabetes) | Phase III |
| prosaptide TX14(A) | Myelos Neurosciences San Diego, CA | growth factor | neuropathic pain and peripheral neuropathy | Phase II |
| Rebii ® recombinant interferon beta-1a | Serono Laboratories Norwell, MA | interferon | relapsing, remitting multiple sclerosis; transitional multiple sclerosis (see also cancer, infectious diseases) | application submitted |
| ReoPro ® abciximab | Centocor Malvern, PA Eli Lilly Indianapolis, IN | MAb | stroke (see also heart) | Phase II |
| Spheramine ™ | Titan Pharmaceuticals S. San Francisco, CA | cellular therapy | Parkinson's disease | Phase I |
| Zenapex ® daclizumab | Hoffmann-La Roche Nutley, NJ Protein Design Labs Mountain View, CA | MAb | tropical spastic paraparesis (model for multiple sclerosis) (see also cancer, eye, skin, transplantation | Phase I/II |
| | | RESPIRATORY DISEASES | | |
| AAV CFTR gene therapy | Targeted Genetics Seattle, WA | gene therapy | sinusitis (see also genetic) | Phase I |
| acellular pertussis vaccine | Chiron Emeryville, CA | vaccine | pediatric pertussis (whooping cough) | application submitted |

TABLE A-continued

| | | | | |
|---|---|---|---|---|
| anti-IgE humanized MAb | Genentech S. San Francisco, CA Novartis Pharmaceuticals East Hanover, NJ Tanox Biosystems Houston, TX | MAb | allergic asthma allergic rhinitis | Phase III Phase II |
| Influenza rHAO Vaccine influenza vaccine | Protein Sciences Meriden, CT | vaccine | prevention of influenza | Phase II |
| influenza virus vaccine (live, attenuated) | Aviron Mountain View, CA | vaccine | prevention of influenza | Phase III |
| interleukin-4 receptor | Immunex Seattle, WA | recombinant soluble receptor | asthma | Phase I |
| interleukin-10 (IL-10) | Schering-Plough Madison, NJ | interleukin | acute lung injury (see also AIDS/HIV, autoimmune, digestive, heart, neurologic, skin) | Phase I |
| Iisolylline | Cell Therapeutics Seattle, WA | | acute lung injury (see also other) | Phase II |
| NEUPOGEN ® Filgrastim (rG-CSF) | Amgen Thousand Oaks, CA | colony stimulating factor | multilobar pneumonia, pneumonia sepsis (see also AIDS/HIV, cancer) | Phase III |
| Oxsodrol ® rhCuZr super dismutase | bio-Technology General Iselin, NJ | dismutase | bronchopulmonary dysplasia in premature infants | Phase III |
| parainfluenza type-3 vaccine (live, attentuated bovine) | Aviron Mountain View, CA | vaccine | prevention of parainfluenza type-3 infection (cause of croup in infants) | Phase II |
| PIV vaccine, live, attentuated | Wyeth-Lederle Vaccines & Pediatrics Philadelphia, PA | continuous cell line vaccine | prevention of parainfluenza virus-mediated lower respiratory disease in infants | Phase I |
| Quillerimmune-F | Aquila Biopharmaceuticals Worcester, MA | vaccine | pneumococcal infections in the elderly | Phase II |
| recombinant platelet activating factor-acetylhydrolase (rPAF-AI-1) | ICOS Bothell, WA | | acute respiratory distress syndrome, asthma (see also digestive) | Phase II |
| RSV subunit vaccine | Wyeth-Lederle Vaccines & Pediatric Philadelphia, PA | continuous cell line vaccine | prevention of respiratory syncytial virus-mediated lower respiratory disease in the elderly and at-risk children | Phase II |
| RSV vaccine, live, attenuated | Wyeth-Lederle Vaccines & Pediatrics Philadelphia, PA | continuous cell line vaccine | prevention of respiratory syncytial virus-mediated lower respiratory disease in infants | Phase I |
| soluble ICAM-1 (BIRR4) | Boehringer Ingelheim Pharmaceuticals Ridgefield, CT | recombinant soluble receptor | prevention and/or treatment of rhinovirus-induced common cold | Phase II |
| Synagis ™ MEDI-493 humanized RSV MAb | Mediummune Gaithersburg, MD | MAb | prevention of respiratory syncytial virus disease | application submitted |
| TP10 | T Cell Sciences Needham, MA | recombinant soluble receptor | acute respiratory distress syndrome (see also heart, transplantation) | Phase II |
| truncated ICAM | Bayer Berkeley, CA | adhesion molecule | rhinovirus-associated exacerbations of asthma | Phase I |
| SKIN DISORDERS | | | | |
| anti-CD11a humanized MAb (hu1124) | Genentech S. San Francisco, CA XOMA Berkeley, CA | Mab | moderate to severe psoriasis | Phase II |
| gamma interferon | Connetics Palo Alto, CA | interferon | iceloids | Phase II |
| ICM3 | ICOS Bothell, WA | Mab | psoriasis | Phase I |
| IL-2 fusion protein $DAB_{389}IL-2$ | Seargen Hopkinton, MA | fusion protein | moderate to severe psoriasis (see also autoimmune, cancer) | Phase I/II |
| interleukin-10 (IL-10) | Schering-Plough Madison, NJ | interleukin | psoriasis (see also AIDS/HIV, autoimmune, digestive, heart, neurologic, respiratory) | Phase I |
| IR 502 therapeutic vaccine | Immune Response Corp. Carlsbad, CA | vaccine | psoriasis | Phase II |
| ISIS 2302 | Isis Pharmaceuticals | antisense | psoriasis | Phase II |

TABLE A-continued

| | Carlsbad, CA | | (see also autoimmune, digestive, transplantation) | |
|---|---|---|---|---|
| keratinocyte growth factor-2 (KGF-2) | Human Genome Sciences Rockville, MD | growth factor | wound healing (see also other) | Phase I |
| LFA3TIP | Biogen Cambridge, MA | recombinant T-cell inhibitor | psoriasis | Phase II |
| Regranex ™ becaplernin (recombinant human platelet-derived growth factor-88) | Chiron Emeryville, CA R. W. Johnson Pharmaceutical Research Institute Raritan, NJ | growth factor | pressure ulcers (see also other) | Phase III |
| T4N5 Liposome Lotion T4 endonuclease V encapsulated in liposomes | Applied Genetics Freeport, NY | | protection against actinic keratoses in patients with xeroderma pigmentosa | Phase III |
| TGF-beta3 | OSI Pharmaceuticals Uniondale, NY | growth factor | impaired wound healing (see also other) | Phase II |
| transforming growth factor-beta-3 | Novartis Pharmaceuticals East Hanover, NJ | growth factor | wound healing | Phase II |
| Zenapax ® daclizumab | Hoffmann-La Roche Nutley, NJ Protein Design Labs Mountain View, CA | MAb | psoriasis (see also cancer, eye, neurologic, transplantation) | Phase I/II |
| | | TRANSPLANTATION | | |
| allogeneic hematopoietic stem cells | SyStemix Palo Alto, CA | cellular therapy | correct genetic diseases by in utero transplantation of genetically unaffected cells from a sibling or parent | Phase I |
| CBL antibody (ABX-CBL) | Abgenix Foster City, CA | Mab | graft versus host disease | Phase II |
| CTLA4Ig | Bristol-Myers Squibb Princeton, NJ | recombinant soluble receptor | immunosuppression | PHase II |
| HSD-Tk retroviral vector | Genetic Therapy Gaithersburg, MD SyStemix Palo Alto, CA | gene therapy | treatment of graft versus host disease in allogeneic hematopoietic stem cell transplantation | Phase I |
| HSV-tk | Chiron Emeryville, CA | gene therapy | graft versus host disease in bone marrow transplantation | Phase I |
| ISIS 2302 | Isis Pharmaceuticals Carlsbad, CA | antisense | renal transplant rejection (see also autoimmune, digestive, skin) | Phase II |
| LDP-01 | LeukoSite Cambridge, MA | MAb | kidney transplantation (see also neurologic) | Phase I/II |
| MEDI-507 (humanized MAb) | Medimmune Gaithersburg, MD BioTransplant Charlestown, MA | MAb | graft versus host disease acute kidney transplant rejection | Phase II Phase I/II |
| ORTHOCLONE OKT4A | Ortho Biotech Raritan, NJ | MAb | prevention of organ transplant rejection (see also autoimmune) | Phase II |
| Simulect basiliximab | Novartis Pharmaceuticals East Hanover, NJ | MAb | transplantation | application submitted |
| SMART ™ Anti-CD3 HuM291 | Protein Design Labs Mountain View, CA | MAb | organ transplantation (see also autoimmune) | Phase I |
| TP10 | T Cell Sciences Needham, MA | recombinant soluble receptor | transplantation (see also heart, respiratory) | Phase I/II |
| Zenapax ® daclizumab | Hoffmann-La Roche Nutley, NJ Protein Design Labs Mountain View, CA | MAb | liver transplantation (see also cancer, eye, neurologic, skin) pediatric kidney transplantation | Phase II Phase I/II |
| Zenapax ® daclizumab and Cellcept ® | Hoffmann-La Roche Nutley, NJ Protein Design Labs Mountain View, CA | MAb | kidney transplant rejection, cyclosporine elimination | Phase I/II |
| | | OTHER | | |
| Recomburmin recombinant human albumin | Centeron King of Prussia, PA | | excipient use | Phase I |
| Regranex ™ becaplermin (recombinant | Chrion Emeryville, CA R. W. Johnson | growth factor | venous ulcers (see also skin) | Phase III |

TABLE A-continued

| human platelet-derived growth factor-88) | Pharmaceutical Research Institute Raritan, NJ | | | |
|---|---|---|---|---|
| rhBMP-2 | Genetics Institute Cambridge, MA | growth factor | bone and cartilage repair | in clinical trials |
| Saizen ® somatropin (rDNA origin) for injection | Serono Laboratories Norwell, MA | human growth hormone | chronic renal failure in children (see also growth disorders) post-operative recovery | Phase III Phase II |
| Serostint ™ somatropin (rDNA origin) for injection | Serono Laboratories Norwell, MA | human growth hormone | metabolic conditions (see also cancer) | Phase II |
| Somatokine ® recombinant insulin-like growth factor-1/ binding protein-3 | Celtrix Pharmaceuticals Santa Clara, CA | growth factor | hip fractures, severe acute burns | Phase II |
| TGF-beta3 | OSI Pharmaceuticals Uniondale, NY | growth factor | oral mucositis (see also skin) | Phase II |

The content of this survey has been obtained through government and industry sources based on the latest information.
Survey current as of Mar. 13, 1998. The information may not be comprehensive. For more specific information about a particular product, contact the individual company directly.
PhRMA Internet address: http://www.phrma.org
Provided as a Public Service by PhRMA. Founded in 1958 as the Pharmaceutical Manufacturers Association.
Copyright © 1998 by the Pharmaceutical Research and Manufacturers of America. Permission to reprint is awarded if proper credit is given.

In one aspect, particular benefit is obtained with this invention when used with biopharmaceuticals, which include, for example, any proteins, polypeptides, enzymes, immunoglobulins, polynucleic acids, and plasmids or other biopolymers. Specific examples of biopharmaceuticals to be included in the crystal formulations of the present invention include the following: insulin, glucagon, Glucagon-Like Peptide-1 (7-37)OH (GLP-1), human growth hormone, leptin, follicle-stimulating hormone (FSH), ribozyme, and analogs thereof.

The API's useful with the present invention include those which themselves may form crystalline products, as well as those which do not. By way of example, any proteins can be prepared as microcrystalline suspension products, but the results have frequently been unsatisfactory using existing technology. However, inclusion of these biomolecules into a host crystal system in accordance with the present invention overcomes this limitation on crystallization. The invention further finds utility even with API's that are readily crystallized, such as insulin. The incorporation of such API's into a single crystal lattice can be used to enhance stability or provide means of delivery that have different characteristics.

Solvents for preparation of the saturated and supersaturated crystal lattice component include, but are not limited to, water alcohols (e.g., ethanol, isoproponal), other organic solvents, acids, bases, and buffers.

The crystals of the present invention are prepared to have a predetermined amount of active pharmaceutical ingredient. The desired amount of active pharmaceutical ingredient will depend on typical considerations, such as the effective amount of API used for administering to a patient. The concentration of API in the crystal is controlled, such as by previously described means, to yield crystals which are readily used in preparing pharmaceutical formulations for administration. The active pharmaceutical ingredient can be incorporated into the crystals at any of a wide variety of molar or weight percentages. Preferred percentages can be easily selected by a skilled artisan taking into account the usual considerations for later formulation of the desired pharmaceutical compositions, depending on the application, route of delivery, and desired pharmacological profile. Preferred percentages include, for example, concentrations of 0:01–1 weight percent. As used herein, all weight percentages are given as the percent based on the weight of the crystal including the crystal lattice component, the active pharmaceutical ingredient and any other components included within the crystals, unless stated otherwise.

The crystals may be prepared at varying size distributions, similarly depending on the subsequent formulating to be done with the crystals, or on crystal growth parameters. The crystals may be harvested and then sorted directly to desired size ranges, or may first be processed, such as by grinding or milling, and then sorted such as by sieving. As will be appreciated, a desired amount of active pharmaceutical ingredient may be obtained simply by obtaining a determined weight of crystals containing the active pharmaceutical ingredient at a known weight concentration. The useful size or weight range of the crystals of the present invention accordingly varies widely, depending on such factors as the inclusion level of the active pharmaceutical ingredient, the dosage amount for the active pharmaceutical ingredient, and the method of delivery of the crystals. By way of example, suitable crystals may have an average size distribution of 1 $\mu$m to 1 mm.

The crystals of the present invention will typically be used in a formulation comprising a large number of crystals. It is a feature of the present invention that the active pharmaceutical ingredient is included within the crystal lattice component in a predictable, oriented fashion. This leads to a uniform concentration of the active pharmaceutical ingredient as a molar, and therefore weight, percentage of the crystals. In one aspect of the present invention, there is provided a composition of crystals having a substantially uniform weight concentration of active pharmaceutical ingredient as between crystals. The term "substantially uniform weight concentration" refers to the fact that the weight concentration of active pharmaceutical ingredient in the various crystals is sufficiently uniform that an acceptably accurate weight of active pharmaceutical ingredient can be obtained based on the weight of the crystals and the average concentration of active pharmaceutical ingredient in such crystals. In one preferred embodiment, there is provided a composition of crystals in which the size distribution of active pharmaceutical ingredient does not vary between crystals by more than about 20 percent. However, alternate embodiments may be equally useful, including mixtures of different size crystals. A desired quantity of active pharmaceutical ingredient is then accurately obtained by measuring a weight amount of crystals which, given the concentration of active pharmaceutical ingredient, yields the selected weight of active pharmaceutical ingredient.

The crystals and included API's are useful in the crystal form for both the stabilization and storage of the API and for the administration of the API to a patient. As used herein, it will be appreciated that the term patient refers to either humans or non-humans, depending on the nature of the active pharmaceutical ingredient. The crystals may be used as such, and in one aspect of the present invention the crystals consist essentially of simply the crystal lattice component and the API. Alternatively, the crystals include the crystal lattice component and the API in combination with other pharmaceutically-acceptable adjuvants also contained within the crystals.

The crystals of the present invention are preferably formulated as pharmaceutical materials for ultimate delivery in solid or liquid form. In such applications, the crystals are typically formulated with common, compatible, pharmaceutically-acceptable adjuvants, such as excipients, diluents, carriers or mixtures thereof. For purposes herein, the term "pharmaceutically-acceptable" refers in this context to the excipients, diluents or carriers, as well as coatings or other components referred to elsewhere, being compatible with the other ingredients of the formulation and no deleterious to the recipient thereof.

Examples of excipients, diluents, and carriers that are suitable for such dosage forms are well known in the art, and include the following: suspension additives such as tonicity modifiers, buffers, precipitants, and preservatives; fillers and extenders such as starch, lactose, dextrose, sucrose, sorbitol, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol and glycerol monostearate; adsorptive carriers such as kaolin and bentonite; and lubricants such as talc, calcium and magnesium stearate, and solid polyethyl glycols. Additionally, the adjuvant may comprise crystals of the crystal lattice component that are prepared without the included API.

The crystals may be coated to achieve various effects. In one approach, the crystals are coated with the same crystal lattice component which forms the underlying crystal, but without the include API. This assures that the coating and the underlying crystal have compatibility. The coating is then applied at a thickness which provides the desired effect, such as further protection of the active pharmaceutical ingredient, bulking of the crystal for handling, and/or effecting a sustained or delayed release of the active pharmaceutical ingredient. Alternatively, the same effects can be accomplished by coating the crystals with other compatible coating compositions, such as those which are well known in the pharmaceutical coating art. The crystals can also be coated so as to release the active pharmaceutical ingredient only or preferably in a particular part of the intestinal tract or other route of administration, possibly over a period of time. This is accomplished, in known fashion, using coatings, envelopes, and protective matrices made, for example, from polymeric substances or waxes.

It is a feature of one aspect of the present invention that the crystals and included API's may be packaged and administered to patients in discrete pharmaceutical dosage forms. The crystals may be used as such in solid form, or may be formulated into liquid solutions or suspensions prior to use. The compositions may accordingly be administered by various routes, for example, by the oral, rectal, vaginal, ocular, buccal, nasal, pulmonary, iontophoretic, topical or parenteral routes. Such compositions form part of the present invention and are prepared in manners well known in the pharmaceutical art.

The API's of the present invention are effective over a varied dosage range. Such dosages are readily accommodated by the present invention by permitting various sizes of crystals, concentrations of API, etc. It will be understood that the amount administered will be determined in light of the relevant circumstances, including the condition to be treated, the choice of API to be administered, the size of the patient being treated, and the chosen route of administration. Therefore, specific dosage ranges will differ accordingly, and are not limiting of the scope of the invention in any way.

The compositions are formulated in one embodiment as a unit dosage form. The term "unit dosage form" refers to physically discrete units, such as tablets, capsules, and suspensions in vials or cartridge/pen systems suitable as unitary dosages, particularly as unitary daily dosages. Each discrete unit contains a predetermined quantity of active pharmaceutical material calculated to produce the desired effect, e.g., a prophylactic or therapeutic effect. The amount of active pharmaceutical ingredient contained in a given dosage unit can be varied depending on the manner of delivering the crystals. For example, a single dosage unit in tablet form may contain ¼, ⅓, ½ or 1 times the unit dose for the active pharmaceutical ingredient, according to which 1 to 4 tablets would be administered to achieve a unit does of the active pharmaceutical ingredient.

Therefore, in one aspect of the present invention, there is provided a pharmaceutical product in dosage form comprising a pharmaceutical delivery unit including a dosage amount of active pharmaceutical ingredient. The API is contained within the crystal lattice component, and a sufficient amount of crystals is included within the delivery unit to constitute the dosage amount of the API. It will be appreciated that the dosage amount of pharmaceutical may be obtained by provision of one or more crystals of the present invention. One form of the product consists essentially of a dosage amount of the crystals. In an alternative form, the pharmaceutical product consists of the dosage amount of the crystals.

The ultimate delivery forms may include, for example, tablets, soft and hard gelatin capsules, pellets, granules, marumes, lozenges, sachets, cachets, elixirs, suspensions, ointments, suppositories, injection solutions and suspensions, nonpareils, spheres and sterile packaged powders. The crystals may be coated or uncoated, and may be combined with various pharmaceutical adjuvants, including excipients, diluents and carriers, as already described. One preferred form of the pharmaceutical product consists essentially of the crystals, and an alternate form consists of the crystals and the pharmaceutically-acceptable adjuvants. The delivery forms are prepared by conventional techniques such as disclosed in Remington's Pharmaceutical Sciences, 19th Edition, Mack Publishing Company, Easton, Pa. (1995), which is incorporated herein by reference, or other treatises available to the skilled artisan.

Compressed tablets, for example, are prepared by well-known means which are conventional in the art. The tablets may be prepared by wet or dry granulation methods or by direct compression, and may be produced by any of a wide variety of tabletting machines. Tablet formulations usually incorporate diluents, binders, lubricating and disintegrators, as well as the crystals with included API's. Typical diluents include, for example, various types of starch, lactose, mannitol, kaolin, calcium phosphate or sulfate, inorganic salts such as sodium chloride, and powdered sugar. Powdered cellulose derivatives are also useful. Typical tablet binders are substances such as starch, gelatin, and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Certain solid pharmaceutical dosage forms of the present invention, most notably tablets, may be coated in conventional fashion with a wide variety of materials utilizing various processes. Typically, the products of the present invention may be sugar coated or film coated in accordance with well-known techniques. The coatings serve as aesthetic purpose as well as a pratical one. Coatings can mask an unpleasant taste or odor, can increase ease of ingestion by the patient, and can serve to improve the ultimate appearance of the dosage form. Similarly, coatings can protect the product from the effects of air, moisture and light, can improve product identification, and can facilitate handling in packaging and fill lines during manufacture.

Various adjuvants may be included in the coating formulations as is well known in the art. These include, for example, permeability enhancers, plasticizers, antitacking agents and the like. A discussion of coating techniques and adjuvants is presented in U.S. Pat. No. 5,015,480, issued to Childers et al. on May 14, 1991, the pertinent portions of which are hereby incorporated herein by reference. Further information pertinent to coating processes and equipment may be obtained from Remington's Pharmaceutical Sciences, supra.

Tables are often coated with sugar as a flavorant and sealant, or with film-forming protecting agents to modify the dissolution properties of the tablet. The compounds may also be formulated as chewable tablets by using large amounts of pleasant-tasting substances such as mannitol in the formulation, as is now well-established practice. Instantly dissolving tablet-like formulations are also now frequently used to assure that the subject consumes the dosage form, and to avoid the difficulty in swallowing solid objects that bothers some subjects.

A lubricant is used in a tablet formulation to prevent the tablet and punches from sticking in the die of the tabletting machine. The lubricant is chosen from such slippery solids as talc, magnesium and calcium stearate, stearic acid and hydrogenated vegetable oils.

Tablet disintegrators are substances which swell when wetted to break up the tablet and release the crystals. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are used to protect crystals and the included API's from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

The crystals with included API's may similarly be formulated into capsules for administration. Such capsules are prepared utilizing conventional encapsulating methods. A general method of manufacture involves preparing the crystals for use in capsules, such as by milling the crystals to a suitable size. The crystals are blended with desired excipients, diluents or carriers, and the resulting mixture is filled into suitably-sized capsules, typically hard gelatin capsules, using conventional capsule-filling machines. The usual diluents include inert powdered substances such as starch of many different kinds, powdered cellulose, especially crystalline and microcrystalline cellulose, sugars such as fructose, mannitol and sucrose, grain flours and similar edible powers.

When it is desired to administer the crystal formulations as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are also in wide use.

The crystals can also be similarly formulated as elixirs or suspensions for convenient oral administration or for parenteral administration, for instance by intramuscular, subcutaneous or intravenous routes.

The inventive crystals enable the design of sustained-release formulations based upon various factors to yield both the desired amount of active pharmaceutical ingredient and the desired pharmacokinetic profile for delivery of the active pharmaceutical ingredient. Selectively incorporating the active pharmaceutical ingredient into the crystal lattice, e.g., into a specific crystal growth sector, modulates the release profiles and can therefore be used to effect desired pharmacological properties. The choice of the crystal component and the process used to grow the crystals of excipient host and guest active pharmaceutical ingredient can be selected and/or modified to adjust parameters such as the delivery rate of the active pharmaceutical ingredient upon use of the formulation. The active pharmaceutical ingredient is incorporated into the crystal matrix at a selected rate, typically as only a small weight percentage of the overall crystal. The permits moderate and uniform rates of release.

Various approaches may be used to accomplish a delayed or sustained release of active pharmaceutical ingredient from the crystals. In a typical application the crystal of the desired size are combined with a compatible preservative and the mixture is injected subcutaneously or surgically implanted to provide a prolonged payout as the crystals dissolve as a result of contact with the surrounding body tissue and fluid. In one approach, the concentration of the active pharmaceutical ingredient in the crystals is reduced in order to effect a sustained release over time. Alternatively, larger crystals may be used to provide for more prolonged payout of the active pharmaceutical ingredient. In another approach, coatings on the crystals are used to affect the rate of release of the active pharmaceutical ingredient. Such coatings may comprise the same crystal lattice component but without the included active pharmaceutical ingredient, as well as other coating compositions useful for this purpose.

In the alternative, the crystals of the present invention can be used to isolate and/or store the active pharmaceutical ingredient for later reconstitution into solution. The crystals may be stored for extended periods of time prior to reconstitution in view of the added stability accorded the API's by the encompassing crystal lattice component. The crystals are then combined with pharmaceutically-acceptable excipients, diluents or carriers to prepare the solutions for subsequent administration. The crystals are readily dissolved or suspended in appropriate diluents, which may be selected, for example, from the list previously provided with regard to diluents used to initially prepare the crystals.

Such solutions of dissolved crystals provide the active pharmaceutical ingredient free of the previously encompassing crystal lattice component. The solutions are useful, for example, for oral administration, parenteral use, or as suppositories. For parenteral administration, for example, the crystals may be formulated in a pharmaceutically-acceptable diluent such as physiological saline (0.9%), 5% dextrose, Ringer's solution, and the like, along with other additives to reduce the solubility of the crystals in suspension.

The resulting pharmaceutical formulations provide an active pharmaceutical ingredient which is included within the host crystal and has enhanced stability and shelf-life. The present invention therefore satisfies the desire to provide certain pharmaceuticals having an acceptable, room-temperature shelf-life. Depending on the circumstances, particularly the API involved, the desired shelf-life can be as little as one month, or may be at least one year, two years or more. The pharmaceutical molecules are generally isolated from one another and from the environment by the surrounding crystal lattice. The containment of the API in the solid crystal lattice also fixes the conformational orientation. This eliminates most of the potential degradation mechanisms, such as polymerization, oxidation, deamidation and proteolysis, that could otherwise reduce the stability of the pharmaceutical.

Methods demonstrating stability include but are not limited to high-performance liquid chromatography for purity and potency, FT-IR for secondary structure, in-vitro and in-vivo bioassays, and pharmacokinetic profiles.

The crystals of the present invention are readily prepared and are useful in containing the included API in an isolated, oriented position within the lattice. The utility of the present invention is demonstrated in the following examples, which are illustrative in nature, and are not to be considered limiting of the scope of the present invention.

EXAMPLE 1

To demonstrate the potential kinetic stabilization of proteins, green fluorescent protein (GFP) was incorporated into deionized α-lactose monohydrate. GFP was selected because it is known to fluoresce only in its native conformation. Upon denaturation, the interior of the β-barrel of the molecule is exposed and the fluorescence of the p-hydroxybenzylideneimidazolinone chromophore is rapidly quenched. Typical crystal growth conditions involved the addition of 8 volumes of an approximately 1 mg/mL (approximately 37 μmole) solution of GFP in 10 mM tris-HCl, pH8 and 10 mM EDTA to 100 volumes of a supersaturated aqueous solution (approximately 1.15 M) of deionized α-lactose monohydrate. The mixed solution was allowed to stand for 3–4 days at room temperature in a 24-well plate. Crystals were harvested between 1–3 days and displayed a hatchet morphology as shown in FIG. 1 with a broad base (010) further bounded by {100}, {110}, {1–10}, and {0–11}. Small (0–10) and {1–50} faces are also occasionally present. When illuminated with a long wavelength UV lamp, the crystals exhibited a bright green fluorescence localized within a sharply defined pyramid corresponding to the (010) growth sector. This indicates that GFP is selectively recognized and overgrown by the (010) face in preference to the others. More importantly, it is evidence that the GFP is in its native conformation. The level of GFP to lactose is approximately 0.008% (w/w).

Figure 2:
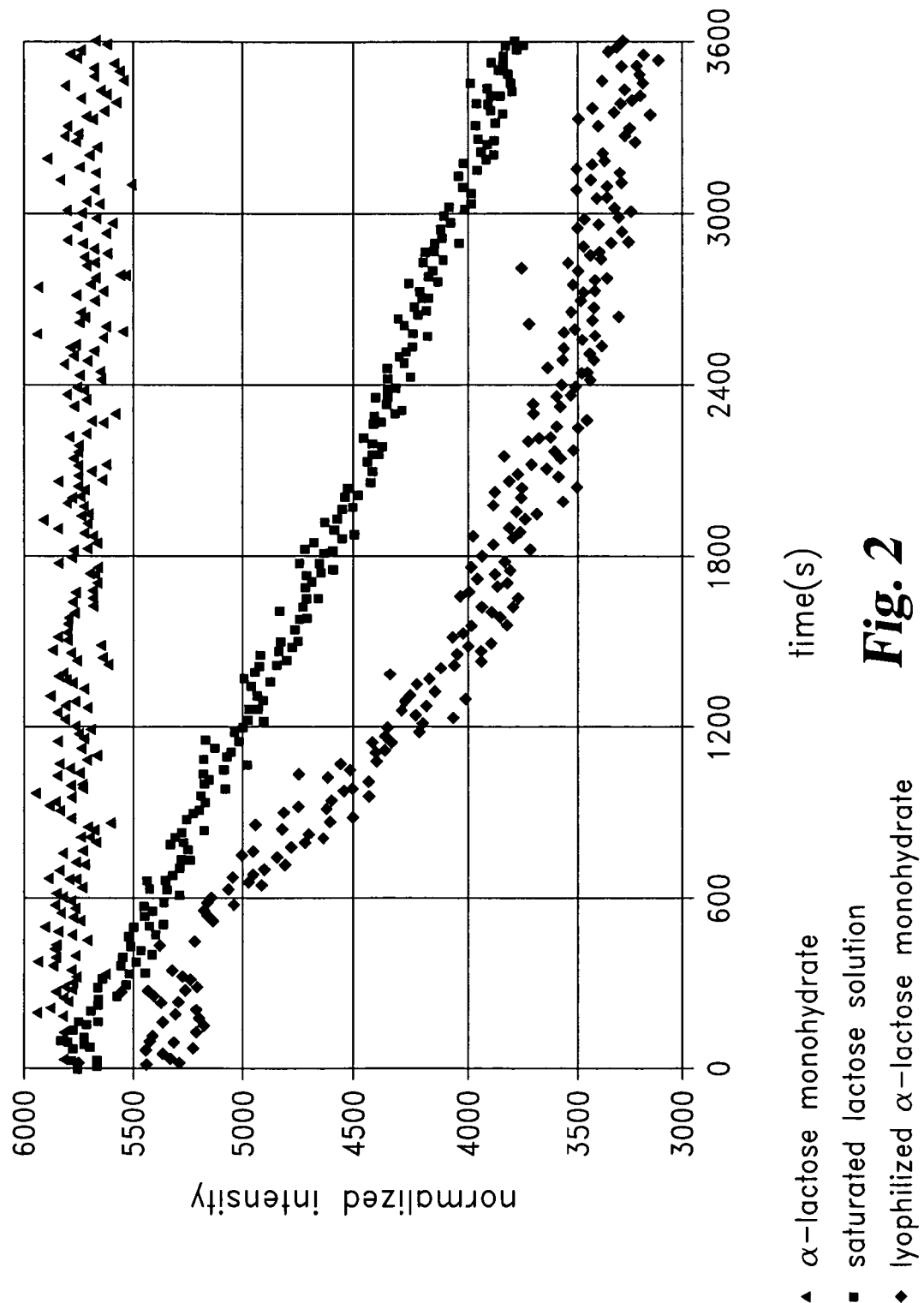
FIG. 2 is a graph of the fluorescence decay of the green fluorescent protein is 333° K. in several environments: mixed crystal in $\alpha$-lactose monohydrate (triangle), saturated lactose solution (square), and lyophilized $\alpha$-lactose monohydrate (diamond).

GFP fluorescence intensity was measured as a function of time and temperature in three environments: saturated aqueous α-lactose solution, lyophilized α-lactose, and crystalline α-lactose monohydrate. As shown in FIG. 2, both the solution and lyophilized preparations lost nearly half of the fluorescence intensity at 333° K. within one hour. The crystal showed no change at 333° K. or even 343° K.

EXAMPLE 2

To investigate the potential for incorporation of a biopharmaceutical into crystals of biocompatible excipients, studies were conducted using rhodamine-labeled glandular glucagon and lactose. As in the previous studies, the rhodamine label was used to facilitate the visualization of glucagon in the host crystals. Typical crystal growth conditions involved the addition of 5 volumes of a supersaturated solution of deionized α-lactose monohydrate to 1 volume of an approximately 1.5 mg/mL (approximately 300 to 400 μmole) of rhodamine-labeled glucagon in purified water. The mixed solution was allowed to stand at room temperature in a 24-well plate. Crystals were harvested between 1–3 days and displayed a hatchet morphology with a broad base. With the rhodamine label, glucagon inclusion was visible in the crystals as a well-defined pyramid corresponding to the (010) growth sector. The level of inclusion was determined to be approximately 0.1% (w/w).

In-vitro dissolution experiments were performed on the glucagon/lactose crystals to evaluate potential for in-vivo, sustained-release pharmacokinetics. The release of rhodamine-labeled glucagon into solution was followed by fluorescence spectroscopy. In a typical experiment, 1–2 crystals were added to 100 microliters of phosphate buffered saline solution at room temperature and the increase in fluorescence of the solution was monitored over time. The release of glucagon from the dissolving crystals was generally complete after 24–48 hours depending on crystal size and was linear until the last few hours of dissolution. Additional details are contained in the article entitled "Stabilization of Proteins in Single Crystal Hosts: Green Fluorescent Protein and α-Lactose Monohydrate," M. Kurimoto, P. Subramony, R. Gurney, S. Lovell, J. A. Chmielewski, B. Kahr, J. Am. Chem. Soc. 1999, 121, 6952–6953, which article is hereby incorporated herein by reference.

EXAMPLE 3

To demonstrate the universality of this technology for incorporation of a diversity of biopharmaceuticals into crystals of biocompatible excipients, studies were conducted using biosynthetic human insulin and insulin analogs, V8-GLP-1(7–37)OH, a glucagon-like insulinotropic peptide-1 analog, exendin, and human growth hormone in deionized α-lactose monohydrate or phthalic acid. Information regarding V8-GLP is available in U.S. Pat. No. 5,705,483, issued to Galloway and Hoffman on Jan. 6, 1998, which patent is hereby incorporated herein in its entirety. For information regarding exendin, see, e.g., R. Goke, H. C.

Fehmann, T. Linn, H. Schmidt, M. Krause, J. Eng, B. Goke, "Exendin-4 is a High Potency Agonist and Truncated Exendin-(9-39)-amide an Antagonist at the Glucagon-like Peptide 1-(7-36)-amide Receptor of Insulin-secreting Beta-cells," J. Biol. Chem. 1993, Sep 15, 268(26), pp. 19650-5, which reference is hereby incorporated herein in its entirety.

Typical crystal growth conditions involved the addition of 1 volume of an approximately 10 mg/mL rhodamine- or Texas red-labeled peptide or protein in 0.1M phosphate-buffered saline solution (PBS, pH7.4) to 10 volumes of a supersaturated α-lactose solution or phthalic acid solution. Supersaturated solutions of purified α-lactose were obtained by adding 0.41 grams of α-lactose to 1 mL of purified water, allowing to dissolve in a 50–70° C. water bath, and cooling to room temperature. Supersaturated solutions of phthalic acid were prepared by adding 0.05 grams of phthalic acid to 1 mL of either 70/30 (v/v) water/acetonitrile or 90/10 water/ethanol, allowing to dissolve in a 50–70° C. water bath, and cooling to room temperature. Larger volumes of supersaturated solutions are obtained by using the same solute-to-solvent ratio.

The solutions of labeled peptide or protein with the supersaturated α-lactose or phthalic acid were mixed by swirling, transferred to a 24-well crystallization plate or other suitable glass or polypropylene container, and allowed to stand at room temperature. Crystals were harvested in 4–5 days and rinsed with hexanes, ethanol, or methanol. All preparations yielded crystals with dye-labeled protein inclusions as determined by microscopic examination using an Olympus SZ-40 microscope with a CCD vision camera.

The shape of the crystals formed was dependent on the solvent system used for the phthalic acid. The crystals formed with phthalic acid in water/ethanol were long, petal-shaped clusters. The crystals formed with water/ethanol were smaller and rhombic. Crystals of labeled-insulin/lactose were dissolved in PBS and analyzed by HPLC. The level of insulin inclusion was determined to be approximately 0.1%. This process is scalable from 100 µL to several liters. The larger volume crystallizations were performed using glass beakers, or other appropriate large containers, covered with watch glasses.

Using the same process, unlabeled insulin and exendin have also been incorporated into α-lactose monohydrate and phthalic acid crystals. Upon dissolution of the crystals with 0.01N HCl, purified water and/or methanol, the level of peptide included in these hosts was determined by analysis of the sample solutions with an HPLC system in the flow-injection analysis mode using a chemiluminescent nitrogen-specific detector (CLND). The level of peptide inclusions ranged from approximately 0.1% to 10% (w/w). These data demonstrate that the level of inclusion can be manipulated by appropriate choice of guest and host molecules in addition to crystallization conditions. See also the following reference which are hereby incorporated herein in their entirety: M. Windholz, (editor). Merck Index, 10$^{th}$ edition, p. 769; R. A. Visser, Neth. Milk Dairy Journal, 34, 1980, pp. 255–275; J. Chmielewski, et al., JACS, 119, 43, pp. 105665–10566.

What is claimed is:

1. A pharmaceutical composition comprising:
   a single crystal of a pharmaceutically-acceptable crystal lattice component; and
   an active pharmaceutical ingredient different from and included within the crystal in a growth-sector specific orientation, the crystal lattice component and the active pharmaceutical ingredient being pharmaceutically pure;
   wherein said crystal lattice component consists essentially of lactose.

2. The invention of claim 1 and further comprising a pharmaceutically-acceptable adjuvant selected from the group consisting of excipients, diluents, carriers and mixtures thereof.

3. The invention of claim 1 in which the active pharmaceutical ingredient is a biopharmaceutical.

4. A pharmaceutical material comprising:
   a mixing of single crystals, each crystal comprising a pharmaceutically-acceptable crystal lattice component and an active pharmaceutical ingredient different from and included within the crystal in a growth-sector specific orientation, the crystal lattice component and the active pharmaceutical ingredient being pharmaceutically pure;
   wherein said crystal lattice component consists essentially of lactose.

5. The pharmaceutical material of claim 4 in which the crystals comprise at least two crystal lattice components, the first crystal lattice component being characterized by first pharmacokinetics and the second crystal lattice component being characterized by second pharmacokinetics.

6. The pharmaceutical material of claim 4 in which said mixture comprises a mixture of two different types of said crystals, the first type of the crystal comprising a first crystal lattice component and the second type of the crystals comprising at least one crystal lattice component different from the first crystal lattice component.

7. The pharmaceutical material of claim 4 in which the active pharmaceutical ingredient comprises discrete units and the units are included within the crystals in isolation from one another.

8. The pharmaceutical material of claim 4 in which the active pharmaceutical ingredient is included within the crystal at a concentration of about 0.001 to 1 weight percent based on the weight of the crystal including the active pharmaceutical ingredient.

* * * * *